(12) United States Patent
Goto et al.

(10) Patent No.: US 11,275,074 B2
(45) Date of Patent: Mar. 15, 2022

(54) BIOPOLYMER ANALYSIS DEVICE AND ANALYSIS SYSTEM

(71) Applicant: HITACHI HIGH-TECH CORPORATION, Tokyo (JP)

(72) Inventors: Yusuke Goto, Tokyo (JP); Takanobu Haga, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 32 days.

(21) Appl. No.: 15/506,090

(22) PCT Filed: Jul. 6, 2015

(86) PCT No.: PCT/JP2015/069422
§ 371 (c)(1),
(2) Date: Feb. 23, 2017

(87) PCT Pub. No.: WO2016/038998
PCT Pub. Date: Mar. 17, 2016

(65) Prior Publication Data
US 2018/0217123 A1    Aug. 2, 2018

(30) Foreign Application Priority Data
Sep. 12, 2014  (JP) .............................. JP2014-186334

(51) Int. Cl.
*G01N 33/487* (2006.01)
*C12Q 1/6869* (2018.01)
*G01N 27/416* (2006.01)

(52) U.S. Cl.
CPC ..... *G01N 33/48721* (2013.01); *C12Q 1/6869* (2013.01); *G01N 27/416* (2013.01)

(58) Field of Classification Search
CPC ........... G01N 33/48721; G01N 27/416; G01N 15/10; C12Q 1/6869; C12Q 1/68
See application file for complete search history.

(56) References Cited

U.S. PATENT DOCUMENTS

2012/0193235 A1 * 8/2012 Afzali-Ardakani .......................... G01N 27/4473
204/601
2013/0161194 A1    6/2013 Jeon et al.

FOREIGN PATENT DOCUMENTS

| JP | 2014-074599 A | 4/2014 |
| JP | 2014074599 A * | 4/2014 |
| WO | 2009020682 A2 | 2/2009 |

OTHER PUBLICATIONS

Reina et al. (JP 2014074599 A, Machine Translation). (Year: 2014).*

(Continued)

*Primary Examiner* — Joshua L Allen
(74) *Attorney, Agent, or Firm* — Miles & Stockbridge, P.C.

(57) ABSTRACT

To slow down the speed of a biopolymer passing through a nanopore during electrophoresis to such a speed that enables a monomer sequence analysis to be performed. A biopolymer analysis device includes two tanks 101*a* and 101*b* each capable of storing a solution containing a biopolymer and an electrolyte, a pair of electrodes 105*a* and 105*b*, a thin film 104 with a nanopore, and a three-dimensional structure 103 disposed on the thin film. The three-dimensional structure has a void that can store a solution, and the void forms a flow channel, the flow channel being adapted to allow the solution to pass therethrough from the nanopore to a portion above the three-dimensional structure, and having on its surface a functional group capable of adsorbing the biopolymer. Thus, when a voltage is applied, the three-dimensional structure is not re-dispersed in the solution at least in the range of a hemisphere having the nanopore as the center and having a biopolymer trapping length r as the radius.

16 Claims, 19 Drawing Sheets

(56) References Cited

OTHER PUBLICATIONS

Vandeventer et al. (PE Vandeventer, JS Lin, TJ Zwang, A Nadim, MS Johal, A Niems, Multiphasic DNA adsorption to Silica Surfaces under Varying Buffer, pH and Ionic Strength Conditions, J. Phys. Chem. B, 116 (2012) 5661-5670). (Year: 2012).*
Wanunu et al. (M Wanunu, W Morrison, Y Rabin, AY Grosberg, A Meller, Electrostatic focusing of unlabeled DNA into nanoscale pores using a salt gradient, Nature Nanotechnology 5 (2010) 160-165). (Year: 2010).*
Rincon-Restrepo et al. (M Rincon-Restrepo, E Mikhailova, H Bayley, G Maglia, Controlled translocation of individual DNA molecules through protein nanopores with engineered molecular brakes, Nano Lett. 11 (2011) 746-750) (Year: 2011).*
Sun et al. (ZQ Sun, X Chen, JH Zhang, ZM Chen, K Zhang, X Yan, YF Wang, WZ Yu, B Yang, Nonsphereical colloidal crystals fabricated by the thermal pressing of colloidal crystal chips, Langmuir 21 (2005) 8987-8991). (Year: 2005).*
Chen et al. (Z Chen, Y Jiang, DR Dunphy, DP Adams, C Hodges, N Liu, N Zhang, G Xomeritakis, X Jin, NR Aluru, SJ Gaik, HW Hillhouse, CJ Brinker, DNA translocation through an array of kinked nanopores, Nature Materials, 9 (2010) 667-675). (Year: 2010).*
Kosiorek et al. (A Kosiorek, W Kandulski, H Glaczynska, M Giersig, Fabrication of nanoscale rings, dots, and rods by combining shadow nanosphere lithography and annealed polystyrene nanosphere masks, Small 1(4) (2005) 439-444). (Year: 2005).*
Venta et al. (K Venta, G Shemer, M Puster, JA Rodriguez-Manzo, A Balan, JK Rosenstein, K Shepard, M Drndic, Differentiation of short, single-stranded DNA homopolymers in solid-state nanopores, ACS Nano, 7(5) (2013) 4629-4636). (Year: 2013).*
Anderson et al. (BN Anderson, M Muthukumar, A Meller, pH tuning of DNA translocation time through organically functionalized nanopores, ACS Nano, 7(2) (2013) 1408-1414). (Year: 2013).*
Zeng et al. (Y Zeng, DJ Harrison, Self-assembled colloidal arrays as three-dimensional nanofluidic sieves for separation of biomolecules on microchips, Anal. Chem. 79 (2007) 2289-2295). (Year: 2007).*
Zhang et al. (H Zhang, J Wirth, Electromigration of single molecules of DNA in a crystalline array of 300-nm silica colloids, Anal. Chem. 77 (2005) 1237-1242). (Year: 2005).*
Fologea, D. et al.; "Slowing DNA Translocation in a Solid-State Nanopore"; vol. 5; No. 9; pp. 1734-1737.
Kowalczyk, S. et al.; "Slowing down DNA Translocation through a Nanopore in Lithium Chloride"; 2012; pp. 1038-1044.
Akahori, R. et al.; "Slowing Single-Stranded DNA Translocation Through a Solid-State Nanopore by Decreasing the Nanopore Diameter"; 2014; 25; 275501; pp. 1-6.
Squires, A. H. et al.; "A Nanopore-Nanofiber Mesh Biosensor to Control DNA Translocation"; 2013; pp. 16304-16307.
Wanunu, M. et al.; "Electrostatic Focusing of Unlabelled DNA into Nanoscale Pores Using a Salt Gradient"; vol. 5; 2010; pp. 160-165.
Rincon-Restrepo, M. et al.; "Controlled Translocation of Individual DNA Molecules Through Protein Nanopores with Engineered Molecular Brakes"; 2011; pp. 746-750.
Office Action dated Jan. 23, 2020 in corresponding British Application No. 1703320.0.
Rena Akahori et al. "Slowing single-stranded DNA translocation through a solid-state nanopore by decreasing the nanopore diameter" Nanotechnology, Abstract, Jun. 2014, vol. 25, No. 27.

* cited by examiner

Condition where Passing Speed is Too High

Condition where Passing Speed is Sufficiently Low

BIOPOLYMER ANALYSIS DEVICE AND ANALYSIS SYSTEM

TECHNICAL FIELD

The present invention relates to a biopolymer analysis method that uses a pore embedded in a thin film and, in particular, to a method for analyzing DNA or protein.

BACKGROUND ART

When a molecule of a biopolymer passes through a pore with a diameter of about 0.9 nm to several nm (hereinafter referred to as a nanopore) that is embedded in a thin film with a thickness of about several Å to several tens of nm, the electrical property of a portion around the nanopore changes in a pattern in accordance with a monomer sequence pattern of the biopolymer. In recent years, a method for analyzing a monomer sequence of a biopolymer using such a phenomenon has been actively researched. A nanopore is often used in such a configuration that a solution containing an electrolyte is provided on each side of a thin film. When a voltage is applied across the front and rear sides of the thin film to generate a potential difference therebetween, the solution containing the electrolyte can be allowed to pass through the nanopore. A method that focuses on an ion current generated at that time as an electrical property and performs an analysis based on the principle that the amount of change in an ion current, which is observed when a biopolymer passes through the nanopore, differs depending on the monomer species is considered as the most promising method (FIG. 2). In addition to the method that uses an ion current, a method of, using a pair of electrodes formed at a nanopore portion and using tunnel current flowing between the electrodes, performing an analysis based on the principle that the amount of tunnel current, which is observed when a biopolymer passes through the nanopore, differs depending on the monomer species is also widely known. None of the above two methods needs a chemical operation involving fragmentation of a biopolymer unlike with the conventional methods, and can directly read a biopolymer. A system in which DNA is a target biopolymer to be analyzed is a next-generation DNA base sequence analysis system, and a system in which protein is a target biopolymer to be analyzed is an amino acid sequence analysis system. Both of such systems are expected as systems that can decode far longer sequences than those in the conventional systems.

Nanopore devices come in two types: one is a biopore device formed by embedding a pore using protein in the center of a lipid bilayer membrane, and the other is a solid pore device obtained by forming a pore in a thin insulating film formed through a semiconductor processing process. In the biopore device, the amount of change in an ion current is measured using a pore (with a diameter of 1.2 nm and a thickness of 0.6 nm) of altered protein (e.g., *Mycobacterium smegmatis* porin A (MspA)) that is embedded in a lipid bilayer membrane, as a biopolymer detection unit. However, as the thickness of the pore is greater than the unit of a monomer molecule (the distance between adjacent nucleic acids that are the monomers of DNA is 0.34 nm), information on a plurality of monomer molecules can be mixed in with the amount of change in an ion current. In addition to such deficiency in the spatial resolution, the use of protein for the pore portion may cause denaturation of the protein depending on the solution conditions or environmental conditions, which can result in the degradation of the device. Thus, there is a problem in that the robustness of the device is low from the viewpoint of stability and life. Meanwhile, the solid pore device can be obtained by forming a pore in a monolayer thin film of graphene or molybdenum disulfide. With the thickness of such a thin film, it is possible to ensure sufficient spatial resolution to read the unit of a monomer molecule. Further, unlike the biopore device formed with protein, the solid pore device has an advantage in that the material is stable under a variety of solution conditions and environmental conditions, and the robustness of the device is thus high. In addition, as the solid pore device can have nanopore portions that are arranged in parallel in a semiconductor processing process, the solid pore device is drawing attention as a device that is more excellent than the biopore device in view of the aforementioned advantages.

As a means for transporting a DNA chain, which is a biopolymer, to a nanopore, a method of electrophoresing a biopolymer using as a driving force a potential difference that generates an ion current is used most widely. However, as illustrated in FIG. 3, as the speed of a DNA chain passing through a nanopore during electrophoresis is very high, it is only possible to obtain a value of a signal containing a mixture of signals of a plurality of monomer molecules. Thus, in order to implement a sequencing analysis, a technique of slowing down the speed of a DNA chain passing through a nanopore is necessary. Specifically, it is preferable to slow down the speed of a DNA chain to a level of greater than or equal to 100 µs/monomer molecule. However, at present, a speed of 0.01 to 1 µs/monomer molecule is realized at the most. Therefore, it is necessary to slow down the speed of a DNA chain by at least about 100 to 10,000 times. If the speed of a DNA chain can be slowed down as described above, a signal of only a monomer molecule can be obtained.

A variety of methods has been devised in order to solve the aforementioned problems. A variety of methods for adjusting the physical properties of a solution has been studied, and for example, a method of increasing the viscosity of a solution by adding high-concentration glycerol thereto and thus increasing a frictional force that acts in a direction opposite to a tractive force that acts on a DNA chain during electrophoresis so as to slow down the speed of the DNA chain passing through a nanopore has been attempted (Non Patent Literature 1). In addition, a method of reducing the apparent negative charge of a DNA chain by adding lithium ions into a solution and thus reducing a tractive force that acts on the DNA chain during electrophoresis so as to slow down the speed of the DNA chain passing through a nanopore has been verified (Non Patent Literature 2).

Other than the method for adjusting the physical properties of a solution, a method for exercising ingenuity on the device side has also been studied. For example, a method for exercising ingenuity on a nanopore has been verified. As a simple method, there is known a method of reducing the diameter of a nanopore so as to increase a frictional force generated during passage of a DNA chain through the nanopore and thus slow down the speed of the DNA chain passing through the nanopore (Non Patent Literature 3). In addition, a method of providing a new structure on a device is also studied. Patent Literature 1 discloses a method of providing obstacles with two-dimensional shapes on a nanopore device having a two-dimensional flow channel formed therein. Specifically, Patent Literature 1 discloses a structure in which nanosized obstacles (e.g., cylinders), which are regularly spaced apart from one another, are provided on the opposite sides of a thin film having a nanopore formed therein. As other examples of the obstacles, gel materials made of polymers, resin, inorganic porous bodies, or beads are explicitly described. Patent Literature 1 describes that when a biopolymer collides with an obstacle during electrophoresis, a frictional force that acts in a direction to interrupt the phoresis is generated, which in turn slows down the speed of the biopolymer passing through the nanopore. Non Patent Literature 4 discloses, as another means for implementing obstacles, providing a structure in which nanowires made of resin materials, which are stacked in layers in random, are provided on the upstream side of a nanopore. Specifically, Non Patent Literature 4 discloses that the speed of a biopolymer passing through a nanopore is slowed down using a frictional force that is generated upon collision of the biopolymer with a nanowire during electrophoresis.

CITATION LIST

Patent Literature

Patent Literature 1: JP 2014-074599 A

Non Patent Literature

Non Patent Literature 1: D. Fologea, et al. Nano Lett., 2005, 5 (9), 1734.
Non Patent Literature 2: S. W. Kowalczyk, et al. Nano Lett., 2012, 12 (2), 1038.
Non Patent Literature 3: R. Akahori, et al. Nanotechnology, 2014, 25, 275501.
Non Patent Literature 4: A. H. Squires, et al. J. A. C. S., 2013, 135 (44), 16304.

SUMMARY OF INVENTION

Technical Problem

The conventional methods have problems in that the effect of slowing down the speed of a biopolymer passing through a nanopore is not sufficient.

As the aforementioned method for adjusting the physical properties of a solution typified by viscosity by adding glycerol or the like thereto, a case where double-stranded DNA is a target biopolymer to be analyzed is disclosed, and the speed of the biopolymer passing through the nanopore is slowed down by about five times at the most after the addition of glycerol. In addition, as an additive also passes through the nanopore during passage of the biopolymer through the nanopore, there is another problem in that the difference between signal values, which differ depending on the monomer species, for each monomer molecular unit becomes small, and thus, detection of the monomer species becomes difficult. As the method of adding lithium ions, a case where single-stranded DNA is a target biopolymer to be analyzed, for example is disclosed, and the effect of slowing down the speed of the biopolymer passing through the nanopore is about 10 times after the addition of lithium ions.

As the conventional method for slowing down the speed of a biopolymer passing through a nanopore using obstacles, a case where double-stranded DNA is a target biopolymer to be analyzed is disclosed, for example, and the effect of slowing down the speed of the biopolymer passing through the nanopore is about 15 times at the most. Therefore, the method for performing an analysis based on the principle of collision of a biopolymer with an obstacle does not have a sufficient effect of slowing down the speed of the biopolymer passing through the nanopore, either.

Therefore, as none of the aforementioned methods can slow down the speed of a biopolymer passing through a nanopore to a level that enables a monomer sequence analysis to be performed, it has been desired to develop another means.

The present invention has been made in view of the foregoing, and it is an object of the present invention to provide a biopolymer analysis system that can significantly slow down the speed of biopolymer passing through a nanopore by introducing a new principle of slowing down the speed, and thus stably analyze a monomer sequence in the biopolymer.

Solution to Problem

As a representative embodiment of the present invention, there is provided a biopolymer analysis device including two tanks each capable of storing a solution containing a biopolymer and an electrolyte; a pair of electrodes disposed in the respective tanks; a thin film having a nanopore, the thin film being disposed between the two tanks so as to allow the two tanks to communicate with each other via the nanopore; and a three-dimensional structure disposed on the thin film. The three-dimensional structure includes a void, and the void forms a flow channel, the flow channel being adapted to allow the solution to pass therethrough from the nanopore to a portion above the three-dimensional structure, and the flow channel having on its surface a functional group capable of adsorbing the biopolymer. When a voltage is applied across the pair of electrodes, the three-dimensional structure is not re-dispersed in the solution at least in a range of a hemisphere having the nanopore as a center and having a biopolymer trapping length as a radius.

In the present specification, the phrase "not re-dispersed" is defined as follows: under a condition where a three-dimensional structure is in contact with a solution, the three-dimensional structure is not partially separated due to solvation, Brownian movement, or electrophoresis when a voltage is applied.

Advantageous Effects of Invention

According to the present invention, the flow channel in the three-dimensional structure has on its surface a functional group that is adapted to adsorb a biopolymer, whereby a biopolymer is thermodynamically adsorbed onto the surface of the flow channel when the biopolymer has approached close to the surface of the flow channel due to electrophoresis or a diffusion process. Such a state of adsorption occurs as the biopolymer is more stable in terms of free energy than when it is solvated or is ionized and freely diffused in the solution. An adsorption force that acts herein is a force that acts in a direction opposite to a tractive force that acts on the biopolymer during electrophoresis. The magnitude of the adsorption force herein can be controlled as appropriate by adjusting the type of the functional group that modifies the surface of the flow channel as well as the solution conditions, and thus, the speed of a biopolymer passing through the nanopore can thus be adjusted to such a speed range that enables a monomer sequence analysis to be performed.

Further, a structure that provides an adsorption force is not re-dispersed in the solution even when a voltage is applied. Accordingly, a stable flow channel shape can be maintained, and a biopolymer analysis device with high robustness that can be used under a variety of solution conditions and environmental conditions can be provided.

Other problems, configurations, and advantageous effects will become apparent from the following description of embodiments.

DESCRIPTION OF EMBODIMENTS

Hereinafter, embodiments of the present invention will be described with reference to the drawings.

Figure 1:
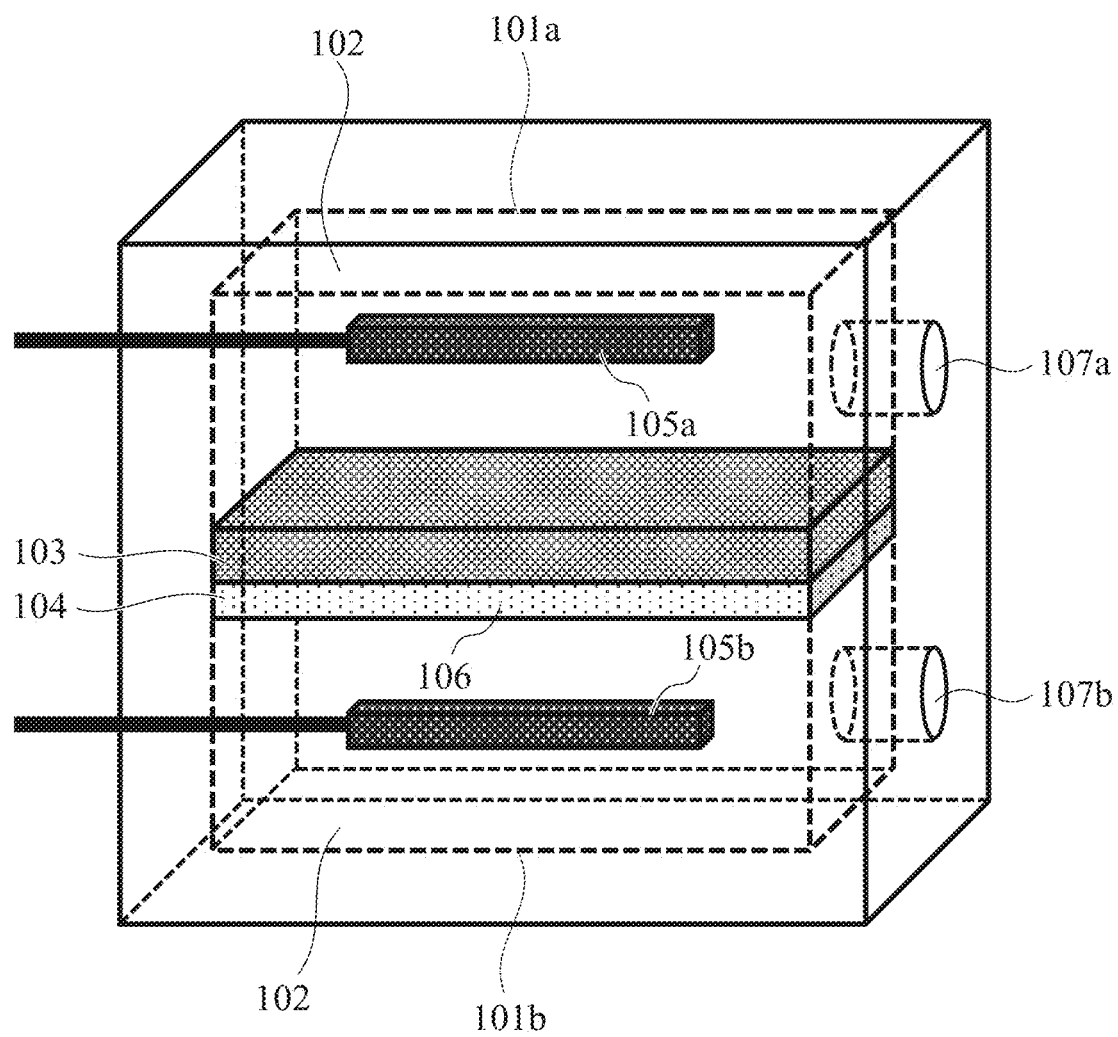
FIG. 1 is a schematic view illustrating an example of a biopolymer analysis device.
Figure 2:
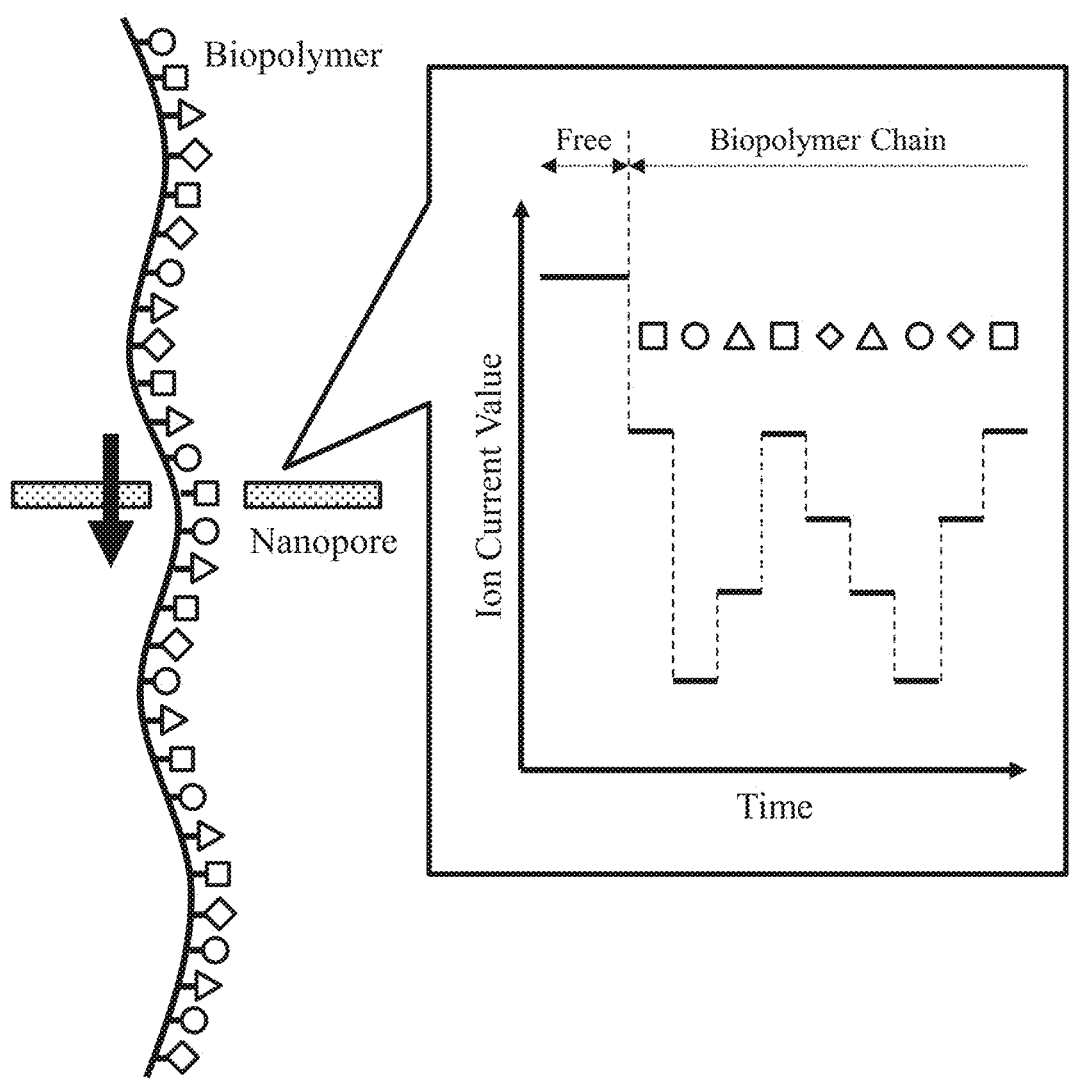
FIG. 2 is a conceptual view of a biopolymer sequence analysis method that is performed based on the principle that the amount of change in an ion current differs depending on the monomer species.
Figure 3:
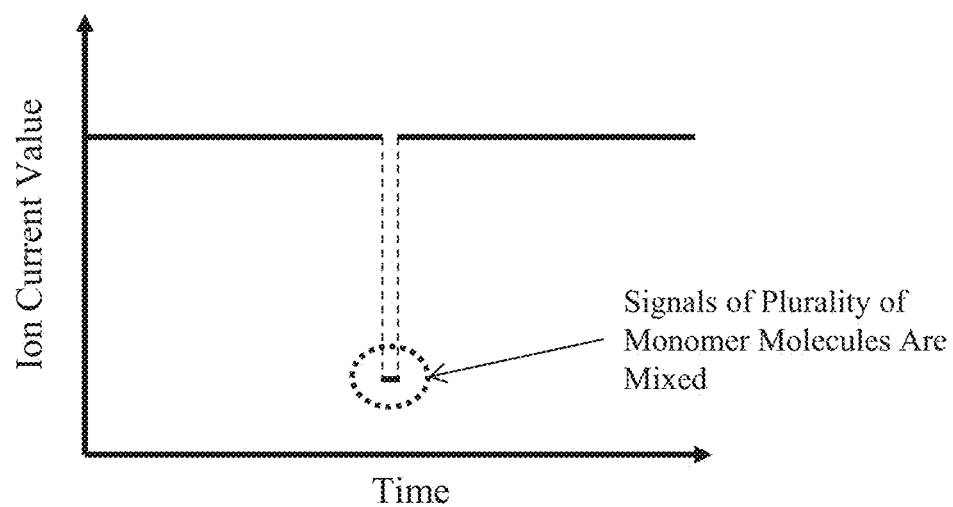
FIG. 3 is a conceptual view illustrating a problem that arises when the speed of a biopolymer passing through a nanopore is a too high.
Figure 3:
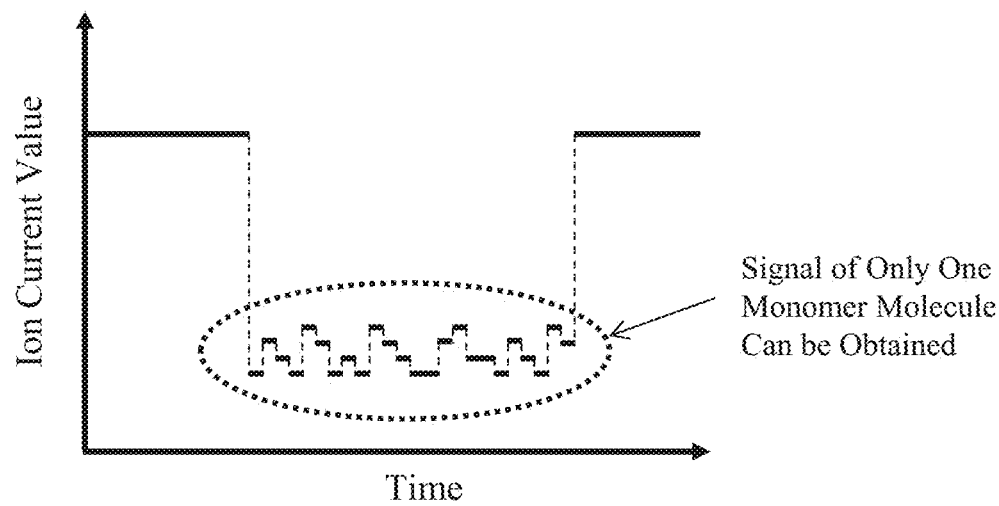

FIG. 1 is a schematic view illustrating an example of a biopolymer analysis device in accordance with the present invention.

Figure 4:
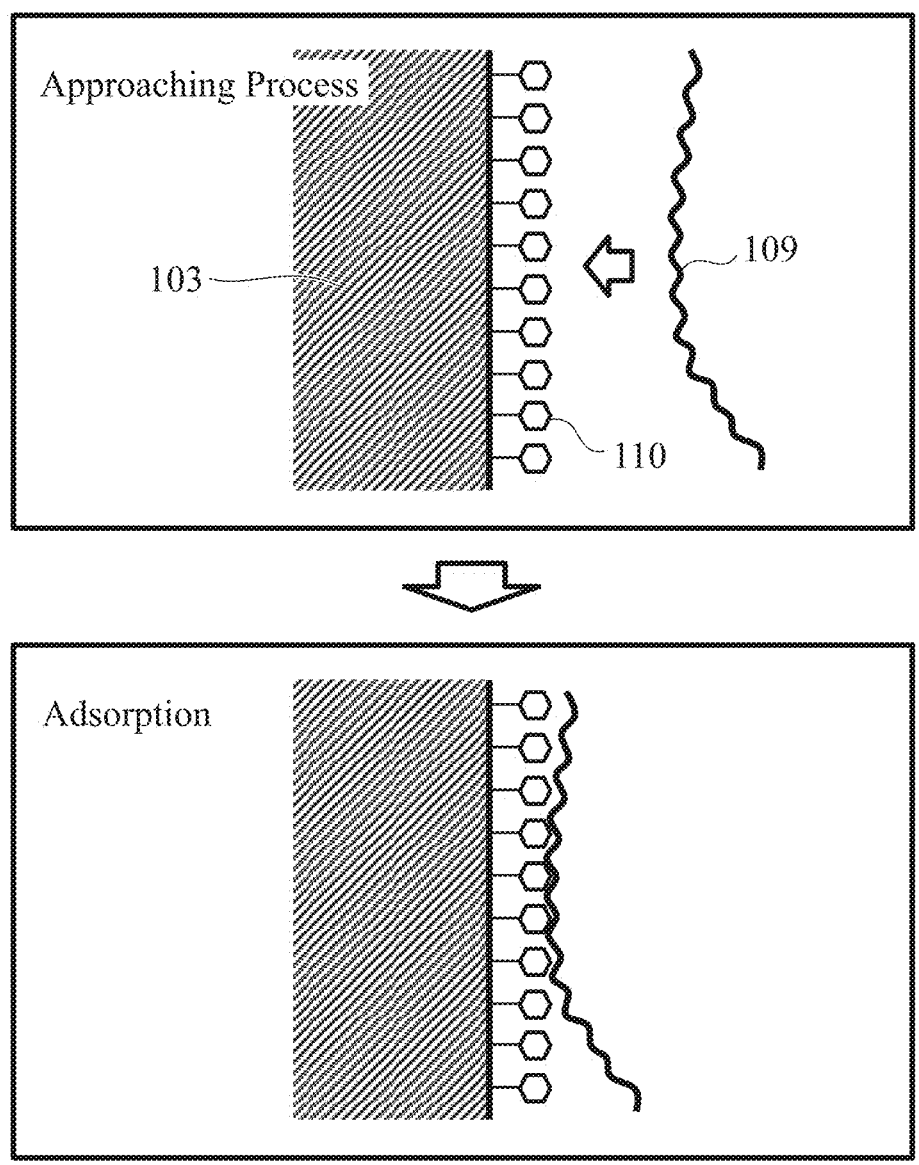
FIG. 4 is a schematic view representing a process of adsorbing a biopolymer.

The present device includes two tanks 101a and 101b each capable of storing a solution 102, a thin film 104 with a nanopore 106 (which will be described in detail below with reference to the drawings of from FIG. 5), a three-dimensional structure 103 disposed on the thin film, and a pair of electrodes 105a and 105b. Each of the solutions stored in the two tanks includes an electrolyte. It is acceptable as long as the solution in at least one of the tanks contains a biopolymer 109. The thin film 104 is disposed between the two tanks 101a and 101b so that the two tanks 101a and 101b communicate with each other via the nanopore 106. As illustrated in FIG. 1, the two tanks preferably have solution inlet ports 107a and 107b, respectively, so as to allow solutions to be introduced thereinto through the solution inlet ports 107a and 107b. However, even when the solution inlet ports are not provided, it is possible to perform measurement of a biopolymer in an open state by dropping some droplets onto the surface of the device. The three-dimensional structure has a void 108 (which will be described in detail below with reference to the drawings of from FIG. 7), and the void serves as a flow channel that allows a solution to pass therethrough from the nanopore to a portion above the three-dimensional structure. As illustrated in FIG. 4, the flow channel has on its surface a functional group 110 that can adsorb a biopolymer. In addition, the three-dimensional structure has such a rigid property that the three-dimensional structure is not re-dispersed in the solution in the range of a hemisphere having the nanopore as the center when a voltage is applied. The radius of the hemisphere herein is a biopolymer trapping length r as defined below.

$$r = \frac{d^2 \mu}{8LD} \Delta V \qquad \text{[Formula 1]}$$

where d is the diameter of the nanopore,

μ is the mobility of a biopolymer during electrophoresis,

L is the thickness of the thin film,

D is the diffusion coefficient of a biopolymer, and

ΔV is a difference in voltages generated between two electrodes.

Examples of a biopolymer include single-stranded DNA, double-stranded DNA, RNA, oligonucleotides, and the like that are formed from nucleic acids as monomers, and polypeptide and the like that are formed from amino acids as monomers. During measurement, a biopolymer preferably has a straight-chain polymer structure with a higher-order structure resolved. Hereinafter, an embodiment in which single-stranded DNA is used as a biopolymer will be described. However, other biopolymers such as those described above can also be applied. As a solvent of the solution, it is most preferable to use water in which a biopolymer can be stably dissolved. Examples of an electrolyte that is contained in the solvent include potassium ions, sodium ions, lithium ions, calcium ions, magnesium ions, fluoride ions, chloride ions, bromide ions, iodide ions, sulfuric acid ions, carbonate ions, nitric acid ions, ferricyanide ions, and ferrocyanide ions. Examples of the material of the electrode include carbon, gold, platinum, and silver-silver chloride, and any electrode that can be used for electrochemical measurement can be used.

The nanopore 106 may have a diameter of about 0.9 nm to 10 nm that is the minimum size that allows single-stranded DNA to pass therethrough, and the thin film may have a thickness of about several Å to several tens of nm. The material of the thin film may be any material that can be formed with a semiconductor microfabrication technique, and typically, silicon nitride, silicon oxide, hafnium oxide, molybdenum disulfide, graphene, or the like can be used. The nanopore can be formed using electron beam irradiation or a pulse-voltage application method. Such methods are disclosed in detail in a document (M. Wanunu, Physics of Life Reviews, 2012, 9, 125.) and a document (I. Yanagi, Scientific Reports, 2014, 4, 5000.).

Examples of the functional group 110 that can adsorb a biopolymer include a silanol group when DNA, RNA, oligonucleotide, or the like is a target biopolymer to be analyzed, for example. It is widely known that a silanol group adsorbs nucleic acids due to the chaotropic effect. A typical example in which glass having a silanol group on its surface is used is disclosed in detail in a document (B. Volgenstein, et al., Proc. Natl. Acad. Sci. USA, 1979, 76, 615.). In order to derive adsorption due to the chaotropic effect, it is acceptable as long as an aqueous solution that contains molecules having the chaotropic effect is used. Preferable examples of molecules having the chaotropic effect include thiocyanate ions ($SCN^-$), dihydrogenphosphate ions ($H_2PO_4^-$), hydrogen sulfate ions ($HSO_4^-$), bicarbonate ions ($HCO_3^-$), iodide ions ($I^-$), chloride ions ($Cl^-$), nitrate ions ($NO_3^-$), ammonium ions ($NH_4^+$), cesium ions ($Cs^+$), potassium ions (K+), guanidium ions, and tetramethylammonium ions. It is known that the chaotropic effect is exhibited more strongly under more acid conditions. Thus, pH of the solution is preferably adjusted to be greater than or equal to pH 1 at which the chaotropic effect is exhibited sufficiently and less than or equal to pH 10 at which the chaotropic effect starts to be exhibited. In addition, it is also known that the chaotropic effect is exhibited more strongly as the ionic strength is higher. Thus, when a solution containing chloride ions is used, for example, the ionic strength of the solution is preferably adjusted to be greater than or equal to 10 mM at which the chaotropic effect starts to be exhibited and less than or equal to the ionic strength (about 3.4 M) of a saturated potassium chloride solution at which the chaotropic effect is exhibited sufficiently. Such solution conditions are described in, for example, a document (P. E. Vandeventer, et al., J. Phys. Chem. B, 2012, 116 (19), 5661.).

Other examples of a functional group that can adsorb a biopolymer include a functional group that is adapted to be ionized into cations. It is known that nucleic acids of DNA, RNA, and the like are negatively charged in an aqueous solution, and thus, they are adsorbed onto positively charged cationic molecules through electrostatic interactions therebetween. Preferable examples of a functional group that is adapted to be ionized into cations include a primary amine group, a secondary amine group, a tertiary amine group, a quaternary amine group, a pyridine group, an imino group, an imidazole group, a pyrazole group, and a triazole group. Although there is a variety of functional groups that are adapted to be ionized into cations, it is preferable to use a functional group that can be stable in an aqueous solution and does not chemically react with a biopolymer. When a functional group that is adapted to be ionized into cations is used, pH of the solution is preferably lower than pKa of the functional group that is adapted to be ionized into cations so that the functional group is stably ionized into cations. For example, pKa of a primary amine group is in the range of 9 to 11, and pKa of ethylamine, which is a representative primary amine, is 10.5. Therefore, when pH of the solution is adjusted to be less than or equal to 10.5, ethylamine can be completely ionized into cations, and thus, DNA and the like can be surely adsorbed onto the surface of the flow channel.

As the flow channel has the functional group on its surface, when a biopolymer has approached close to the surface of the flow channel due to electrophoresis or a diffusion process as illustrated in FIG. 4, the biopolymer is thermodynamically adsorbed onto the surface of the flow channel. Such a state of adsorption occurs as the biopolymer is more stable in terms of free energy than when it is solvated or is ionized and freely diffused in the solution. An adsorption force that acts herein is a force that acts in a direction opposite to a tractive force that acts on the biopolymer during electrophoresis. With such an adsorption force, a tractive force that acts on the biopolymer during electrophoresis can be reduced, thus slowing down the speed of the biopolymer passing through the nanopore. The magnitude of the adsorption force herein can be controlled as appropriate by adjusting the type of the functional group that modifies the surface of the flow channel as well as the solution conditions, and thus, the speed of a biopolymer passing through the nanopore can be easily adjusted to such a speed range that enables a monomer sequence analysis to be performed. A tractive force that acts on DNA due to a potential gradient generated around a nanopore is described in detail in a document (U. F. Keyser, et al., Nature Physics, 2006, 2, 473.), and is known to be 0.24 pN/mV. Meanwhile, with regard to a force of adsorbing a biopolymer, a document (F. Kuhner, Langmuir, 2006, 22, 11180.), for example, describes that a force of adsorbing DNA onto a silanol group was found to be about 55 pN through research conducted using an atomic force microscope. Meanwhile, a document (M. Erdmann, et al., Nature Nanotechnology, 2010, 5, 154.) describes that a force of adsorbing DNA onto a cation group (ionized primary amine group) was found to be about 200 pN through similar research. Therefore, adjusting the tractive force and adsorption force as appropriate can realize a desired speed of a biopolymer passing through the nanopore.

Figure 5:
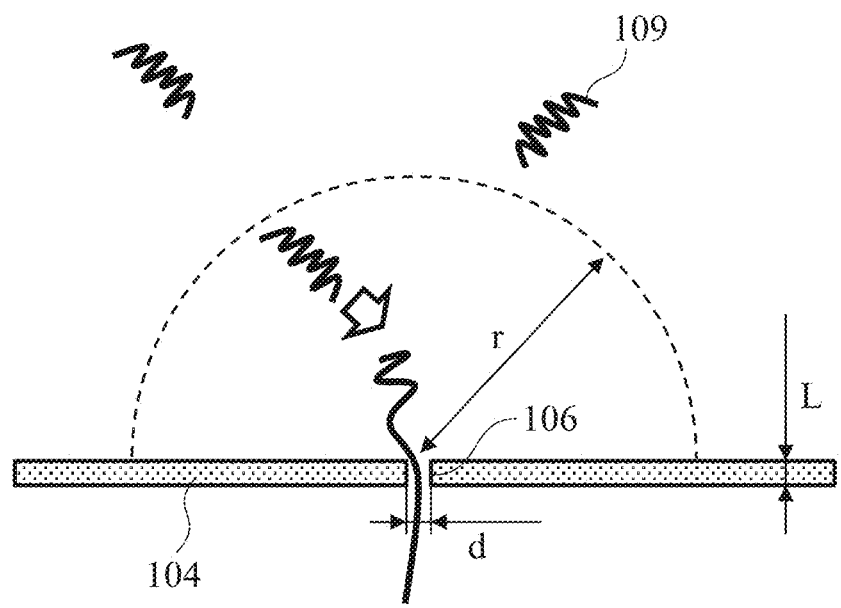
FIG. 5 is an illustration view of a biopolymer trapping length.

The biopolymer trapping length r is the effective distance over which a biopolymer can be transported through electrophoresis using a potential gradient generated around the nanopore (the range of a hemisphere having a radius r) as a drive force as illustrated in FIG. 5. The biopolymer trapping length is defined by Formula 1. The biopolymer trapping length is disclosed in detail in a document (M. Wanunu, et al., Nature Nanotechnology, 2010, 5, 160.). When the biopolymer 109 has approached close to a hemisphere, which has the nanopore 106 as the center and has the biopolymer trapping length as the radius, during a diffusion process, a tractive force that acts on the biopolymer toward the nanopore is generated by electrophoresis. Therefore, in order to slow down the speed of the biopolymer passing through the nanopore, it is essential that the flow channel having a functional group, which can adsorb the biopolymer, be provided in the range of the hemisphere. In addition, in order to realize stable biopolymer detection, it is necessary that the structure have a property such that it is not re-dispersed in the solution in the range of the hemisphere when a voltage is applied. In other words, as a region outside the range of the hemisphere does not contribute to slowing down the speed of the biopolymer passing through the nanopore, it is possible to make an improvement, for example, increase the biopolymer trapping efficiency by limiting the region of the structure as described below.

In order to allow passage of at least a biopolymer, the minimum cross-sectional area of the flow channel needs to be greater than or equal to the cross-sectional area of a molecule of the biopolymer and less than or equal to the maximum cross-sectional area of a portion between voids. A document (K. Venta, et al., ACS Nano, 2013, 7 (5), 4629.) describes that the minimum diameter of a nanopore that allows single-stranded DNA to pass therethrough is 0.9 nm. Therefore, the cross-sectional area of a molecule in this case is 0.81 nm$^2$. In addition, in order to allow a biopolymer to be efficiently adsorbed onto the surface of the flow channel, it is preferable that the maximum cross-sectional area of the flow channel be smaller than a cross-sectional area formed by the mean free path S (dimension is the distance) of the biopolymer as defined by Formula 2.

$$S=\sqrt{Dt} \quad \text{[Formula 2]}$$

where

D is the diffusion coefficient of the biopolymer, and t is the mean residence time of the biopolymer in a portion around the nanopore.

For example, with regard to single-stranded DNA (polythymine with 30 bases), a document (Q. Wang, et al., ACS Nano, 2011, 5 (7), 5792.) describes that the diffusion coefficient of the DNA is 118 μm$^2$/s, and a document (G. Ando, et al., ACS Nano, 2012, 6 (11), 10090.) describes that the mean residence time of the DNA in a portion around a nanopore is 700 ms. According to Formula 2, the mean free path of single-stranded DNA in this case is 9 μm. Therefore, the maximum cross-sectional area of the flow channel, which allows the single-stranded DNA to be adsorbed onto the functional group 110 at least once before it enters the nanopore, is 81 μm$^2$. Accordingly, the cross-sectional area of the flow channel in this case is preferably greater than or equal to 0.81 nm$^2$ and less than or equal to 81 μm$^2$. Herein, a preferable range of the cross-sectional area when single-stranded DNA is a biopolymer to be analyzed is given as an example. However, the range of the cross-sectional area differs depending on a biopolymer to be analyzed or the ion components, viscosity, and the like of the solution used. Thus, the advantageous effects of the present invention can be sufficiently obtained even when the cross-sectional area is outside the aforementioned range.

More preferably, the upper limit of the cross-sectional area of the flow channel is less than or equal to the area of a circle having the biopolymer trapping length as the radius. Limiting the range of the flow channel onto which a biopolymer is adapted to be adsorbed to the range of the biopolymer trapping length can increase the frequency of detection of biopolymers and also reduce the analysis time and analyze biopolymers that are contained in a solution at a low concentration.

When DNA is a target biopolymer to be detected, it is possible to obtain another advantageous effect by setting the upper limit of the cross-sectional area of the flow channel to be less than or equal to the cross-sectional area of molecules of DNA polymerase, DNA helicase, and exosome (with a size of greater than or equal to several nm and less than or equal to several tens of nm). DNA that is extracted from a test body may have the aforementioned protein or structure stuck thereto or mixed therewith as impurities. Therefore, when an analysis is conducted using a nanopore with a size smaller than that of such substances, the substances stuck to the DNA may clog the nanopore while passing through the nanopore, so that the analysis may not be able to be continued. Therefore, limiting the maximum cross-sectional area of the flow channel so as to screen out such substances or allow only DNA without such substances stuck thereto to pass through the nanopore can obtain the effect of executing a smooth analysis.

In addition, limiting the upper limit of the cross-sectional area of the flow channel to be less than or equal to the cross-sectional area of a higher-order structure of DNA can obtain similar advantageous effects. It is known that in the case of DNA with a sequence of consecutive guanine bases, for example, a higher-order structure (tetramer with a size of greater than or equal to 2.6 nm and less than or equal to 10 nm) is formed. Therefore, providing the aforementioned limit can denature the DNA with a higher-order structure into a straight chain or allow only monomers of the DNA to pass through the nanopore, whereby a smooth analysis can be executed.

Figure 6:
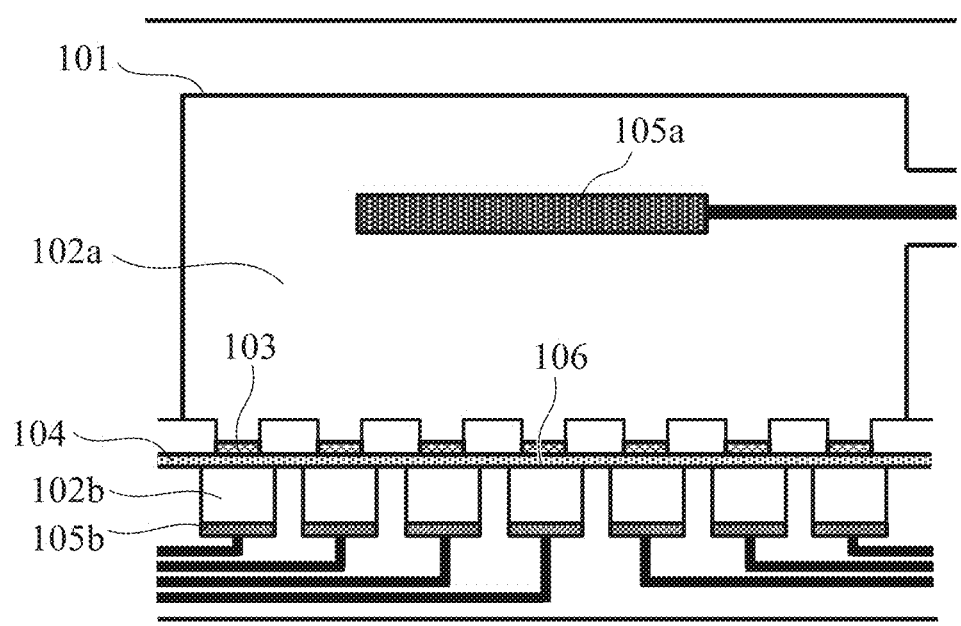
FIG. 6 is a cross-sectional schematic view of a portion around a nanopore illustrating another configuration of a biopolymer analysis device.

FIG. 6 is a cross-sectional schematic view of a portion around a nanopore illustrating another configuration of a biopolymer analysis device in accordance with the present invention. In FIG. 6, a plurality of nanopores are arranged in parallel. When a device is constructed using only a single nanopore as illustrated in FIG. 1, it is acceptable as long as one three-dimensional structure and a pair of electrodes are provided for the nanopore. Meanwhile, when a plurality of nanopores are arranged in parallel to be used as a device as illustrated in FIG. 6, one three-dimensional structure 103 needs to be arranged on a thin film 104, which has nanopores, for each nanopore 106. It is acceptable as long as an electrode (typically, an electrode that is grounded) 105a that is immersed on one solution side is used as a common electrode, while one independent electrode 105b is provided for each nanopore on the other solution side. A solution 102a provided on the common electrode side is a solution that is common to each nanopore 106, while a solution 102b provided on the side opposite to the common electrode needs to be one independent solution that is provided for each nanopore 106. The partition for ensuring the independence of each solution is preferably made of an insulating material. For example, polydimethylsiloxane, silicon oxide, or the like is preferably used. According to such a configuration, biopolymer analyses can be independently executed without being electrochemically interfered with one another, and thus, the throughput of the biopolymer analyses can be increased.

Embodiment 1

Figure 7:
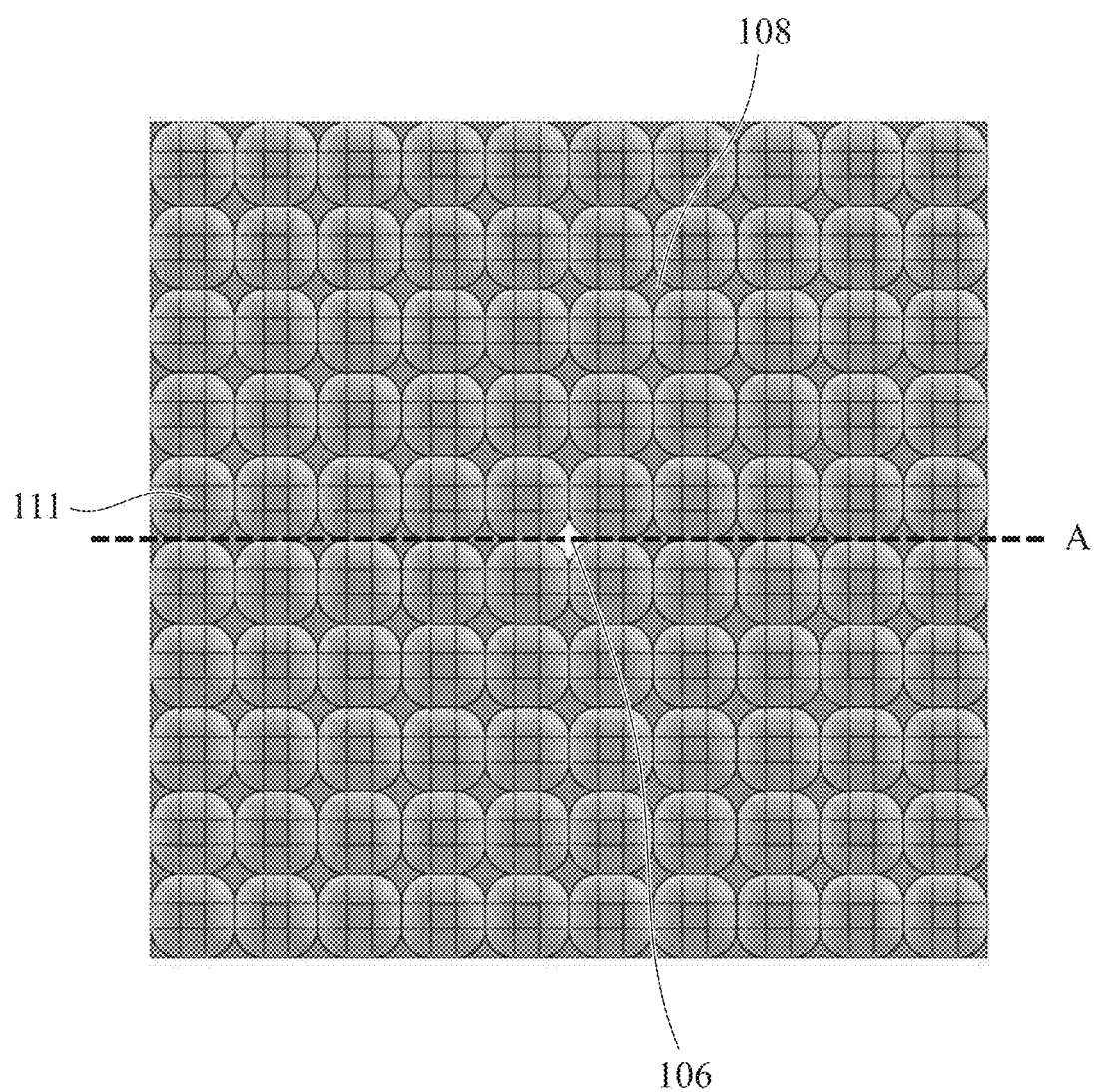
FIG. 7 is a bird's-eye view of a three-dimensional structure in the device.
Figure 8:
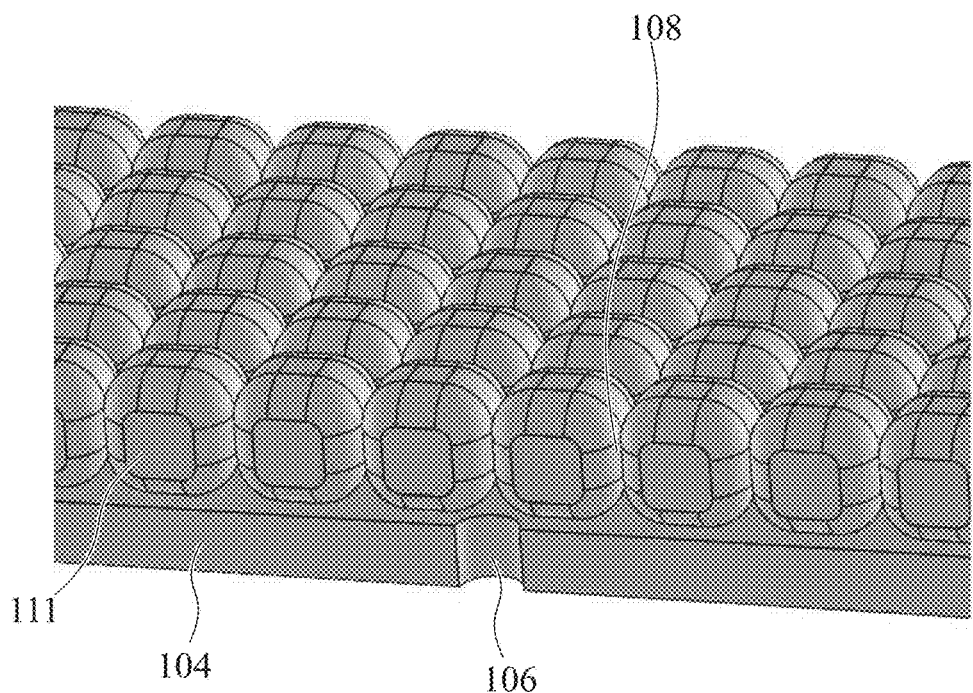
FIG. 8 is a schematic perspective view of a portion around a nanopore representing a three-dimensional structure in the device.
Figure 9:
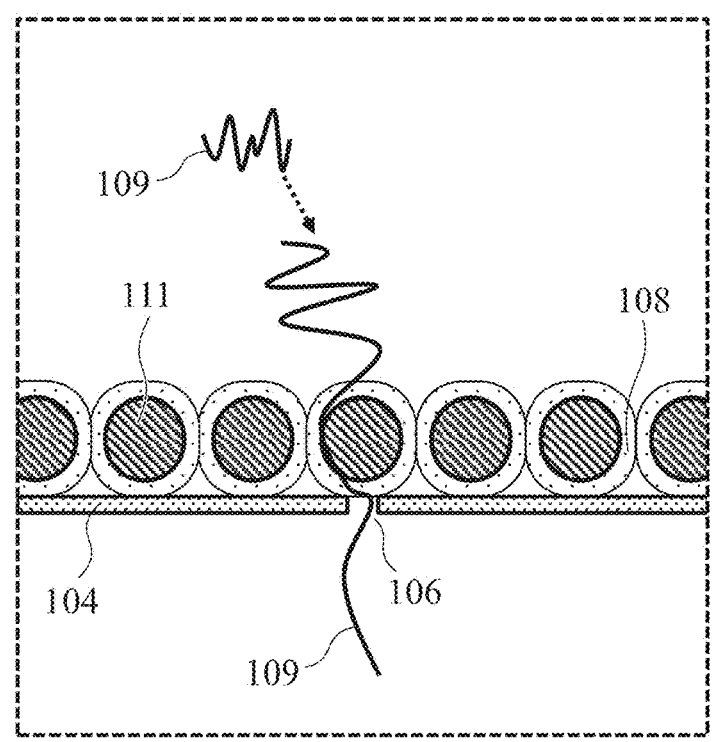
FIG. 9 is a schematic cross-sectional view of a portion around a nanopore representing a three-dimensional structure in the device.

As a configuration of a biopolymer analysis device that realizes a three-dimensional structure with the aforementioned properties, FIG. 7 illustrates a view in which a portion around a nanopore is seen vertically from above the device. FIG. 8 is a schematic perspective view of a portion around the nanopore that is cut along a cross-section A in FIG. 7. FIG. 9 is a schematic cross-sectional view of a portion around the nanopore.

Figure 10:
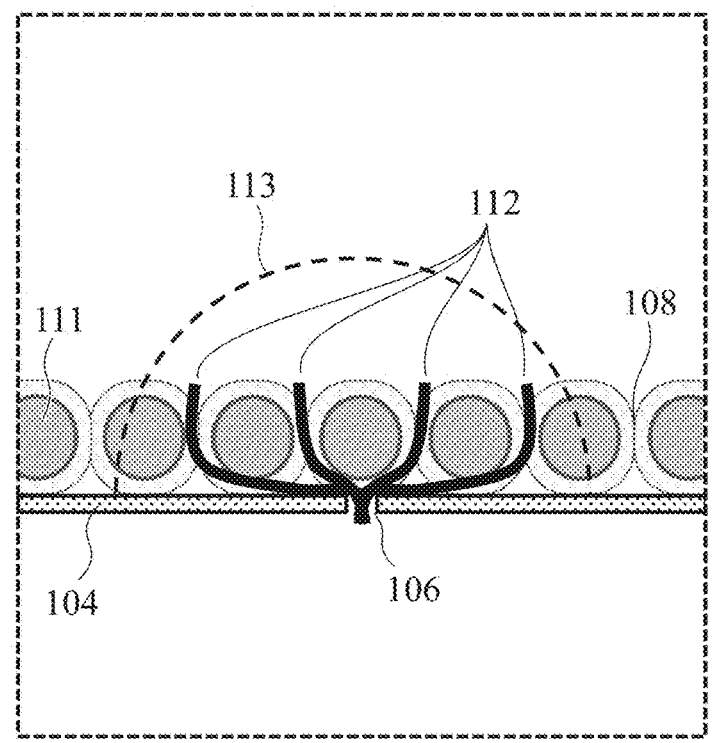
FIG. 10 is a schematic cross-sectional view of a portion around a nanopore in which a flow channel in a three-dimensional structure is represented in an emphasized manner.

This embodiment is characterized in that a three-dimensional structure is molded with a layer of a plurality of particles 111 stacked on a thin film 104. Herein, in FIG. 9, a region indicated by oblique lines is a cross-sectional portion of the molded particles cut along the cross-section A, and annular regions shown in gray are some of the molded particles positioned on the rear side of voids. The voids 108 between the particles form a flow channel 112 through which a solution containing a biopolymer and an electrolyte passes to reach the nanopore. FIG. 10 illustrates the flow channel 112 in bold and emphasized manner. Herein, a potential gradient is generated only in the range of a hemisphere 113 that has the nanopore 106 as the center and has the biopolymer trapping length r as the radius. Therefore, among a number of voids in the present structure, only voids that are located in the range of the hemisphere 113 and are connected to the nanopore 106 can become the flow channel. The surface of each particle is modified by a functional group that can adsorb a biopolymer. The plurality of molded particles have non-spherical shapes so that the particles are not re-dispersed in the solution by being separated from the surface of the thin film in at least the range of the hemisphere due to electrophoresis when a voltage is applied. One advantage of this configuration is that the probability of adsorption of a biopolymer onto the surface of the flow channel can be increased. This is because as the three-dimensional structure is molded with particles, a sufficiently large specific surface area can be provided. As the average diameter of the particles is made smaller, the size of the voids becomes smaller correspondingly, and thus, the probability of adsorption of a biopolymer can be increased. Meanwhile, as the size of the voids is made smaller, the resistance value when ions pass through the voids becomes higher, which in turn decreases the amount of ion current obtained. Thus, a signal value cannot be obtained. Therefore, the probability of adsorption of a biopolymer and the resistance value are in a trade-off relationship. The average diameter of the particles is preferably greater than or equal to 10 nm and less than or equal to 1,000 nm. It should be noted that although a particle may clog the nanopore, in such a case, the particle needs to be in point contact with the nanopore, and such a possibility is quite low. Thus, it is not a practical problem. If there is a nanopore that is clogged by a particle, such a nanopore is not used for an analysis.

Another advantage is that production using particles is easy. When a solution containing particles dispersed therein is applied onto a thin film and only a solvent is evaporated and removed, it is possible to from a three-dimensional structure molded from the particles. As a method for applying a solution, dip coating, spin coating, coating through electrophoresis, or the like can be used. In particular, dip coating, which is not only easy to perform but also can densely arrange particles on the surface of a thin film through self-assembly due to the surface tension of a solvent, is a preferable method. Such a method is disclosed in, for example, a document (X. Ye, et al., Nano Today, 2011, 6, 608.). As a method for evaporating and removing a solvent after applying a solution, a heating evaporation method is preferably used. At this time, selecting suitable materials for the particles can deform the particles. Such a method is disclosed in, for example, a document (A. Kosiorek, et al., Small, 2005, 1, 439.). Before being deformed, the particles only remain in point contact with one another, and the structure is thus an unstable structure that may electrophorese when a voltage is applied. Therefore, the aforementioned deformation process is necessary. Through the deformation process, the particles that have been spherical in shape are pushed against one another and thus deform into non-spherical shapes as illustrated in FIG. 9, so that the particles become into surface contact with one another. Accordingly, the effect of being able to form a stable structure, which can withstand a tractive force that acts on the particles when a voltage is applied, is obtained. The shapes of the particles at this time are desirably polyhedrons so that adjacent particles can be in strong contact with one another. Such polyhedrons can be obtained through thermocompression bonding, and are described in, for example, a document (Z. Q. Sun, et al., Langmuir, 2005, 21 (20), 8987.).

The particles that realize the aforementioned three-dimensional structure need to be selected in view of two points that are moldability and dispersibility in a solution. From the perspective of moldability, a deformable material is desirably used, and for example, resin such as polystyrene or polylactic acid, ceramic such as silica or titanium oxide, or metal such as gold or silver is preferably used. From the perspective of dispersibility in a solution, the particles preferably have high zeta potentials so that the particles can have sufficient repulsion against one another. In particular, the aforementioned silica is a desirable material as its surface is covered with a negatively charged silanol group and thus can realize a sufficiently high zeta potential value for the particles to be independently dispersed in water.

The surface of each particle needs to be modified by a functional group that can adsorb a biopolymer. Such a functional group may be either provided by being applied to the surface of each particle before it is applied to a thin film or provided through a chemical reaction process after it is applied to a thin film.

Another advantage of using a three-dimensional structure that is molded from particles is that a netlike flow channel can be formed. Usually, a biopolymer, in particular, single-stranded DNA has a structure of not a straight chain but a folded Gaussian chain in a solution. Single-stranded DNA with such a shape may be caught in a portion of the thin film while passing through the nanopore, and thus, smooth detection may not be performed. According to this embodiment, a plurality portions in a molecule of single-stranded DNA are adsorbed onto the netlike flow channel, whereby the effect of denaturing the DNA into a straight chain can be obtained. Therefore, smooth detection of a biopolymer through a nanopore is possible.

In order to increase the adsorption efficiency of a biopolymer, it is preferable that the volume occupancy rate of the particles in the three-dimensional structure be higher than the occupancy rate when the particles are in point contact with one another with a closest packed structure. When a single layer of particles is stacked, it is easier to understand the theory based on the area occupancy rate of a figure that is obtained by projecting the three-dimensional structure onto a thin film from right above the three-dimensional structure. In particular, when the particles that are not molded yet have spherical shapes and the centers of the particles of the projected figure form a lattice of an equilateral triangle, the area occupancy rate is preferably greater than $\pi/\sqrt{12}$ that is the theoretical value of point contact. Meanwhile, when the particles that are not molded yet have spherical shapes and the centers of the particles of the projected figure form a lattice of a square, the area occupancy rate is preferably greater than $\pi/4$ that is the theoretical value of point contact.

In the present embodiment, the minimum cross-sectional area of the flow channel refers to the minimum cross-sectional area of voids that form a flow channel connected to the nanopore, among the voids formed between the deformed particles, in the aforementioned range of the hemisphere. Using particles with a particle diameter of greater than or equal to several nm can obtain a cross-sectional area that is greater than or equal to the cross-sectional area of a molecule of the biopolymer. Likewise, the maximum cross-sectional area of the flow channel refers to the maximum cross-sectional area of voids that form a flow channel connected to the nanopore, among the voids formed between the deformed particles, in the aforementioned range of the hemisphere. In addition, the maximum cross-sectional area of the voids refers to the maximum cross-sectional area of all voids formed between the deformed particles in the three-dimensional structure. Therefore, in a region outside the aforementioned range of the hemisphere, the maximum cross-sectional area of the voids can become larger than the maximum cross-sectional area of the flow channel if some of the particles are missing, for example. However, this is not a practical problem as such a portion is a region that does not contribute to the analysis of the biopolymer. This definition is also true for Embodiments 2 to 6 and 9 described below.

Embodiment 2

Figure 11:
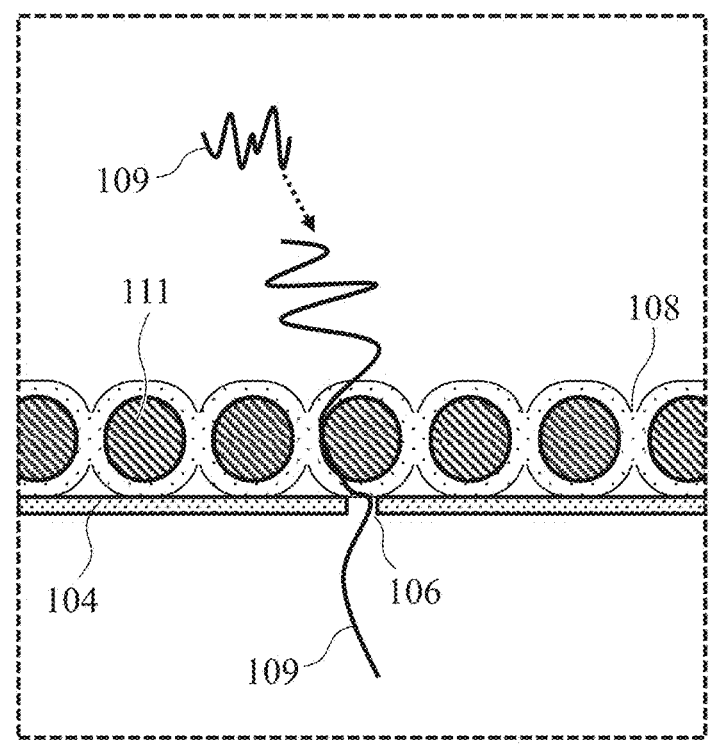
FIG. 11 is a schematic cross-sectional view of a portion around a nanopore of another three-dimensional structure.

FIG. 11 is a schematic cross-sectional view of a portion around a nanopore of a three-dimensional structure with another configuration in a biopolymer analysis device of the present invention. The embodiment illustrated in FIG. 11 is characterized in that adjacent particles in FIG. 9 are integrated.

Although FIG. 9 illustrates an example of a three-dimensional structure with deformed particles, moldability can also be realized by integrating adjacent particles through chemical reaction or through stacking of materials on the surface. For example, if the material of the particles is resin, the resin will plastically deform and the particles will thus contact one another when heated to a temperature of greater than or equal to the glass transition temperature, whereby the molecular chains of the resin can be intertwined with one another and thus integrated. As the resin, polystyrene resin or the like is preferably used. Such a method is described in a document (A. Kosiorek, et al., Small, 2005, 1, 439.). Meanwhile, if the material of the particles is ceramic such as silica or titanium oxide, the particles can be firmly integrated through chemical reaction such as sintering reaction. Such a method of sintering silica particles is described in, for example, a document (T. V. Le, et al., Langmuir, 2007, 23 (16), 8554.). It is also possible to integrate the particles by stacking resin through polymerization reaction by introducing monomers into the voids between the particles. The monomers may be either inorganic or organic. In addition, a similar structure can also be realized by starting surface graft polymerization from the surface of the particles. As another method, there is also known a method of covering the surface of the particles through atomic layer deposition. Integrating the particles has the effect of realizing a stable three-dimensional structure that is not re-dispersed and thus realizing a device with high robustness.

Embodiment 3

Figure 12:
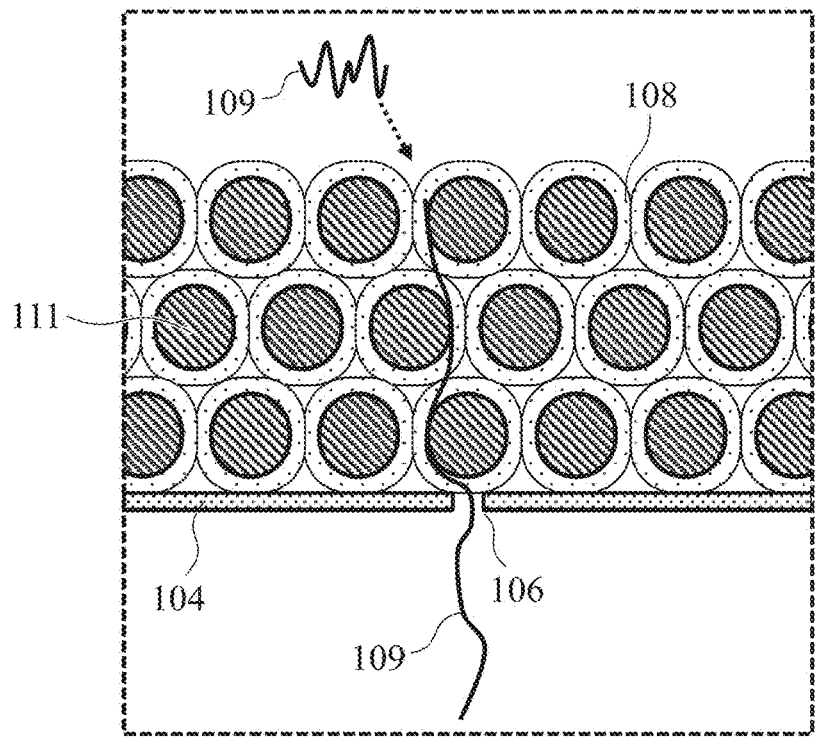
FIG. 12 is a schematic cross-sectional view of a portion around a nanopore of another three-dimensional structure.

FIG. 12 is a schematic cross-sectional view of a portion around a nanopore of a three-dimensional structure with another configuration in a biopolymer analysis device of the present invention. Although FIG. 9 illustrates an example of a three-dimensional structure obtained by stacking a layer of particles, FIG. 12 illustrates an example of a three-dimensional structure obtained by stacking a number of layers of particles. As a number of layers are stacked, the specific surface area is increased correspondingly. Therefore, the aforementioned probability of adsorption of a biopolymer is increased, and the effect of further slowing down the speed of a biopolymer passing through the nanopore is obtained. Further, as the length of the netlike flow channel is further increased, the aforementioned effect of denaturing DNA into a straight chain is further increased, and thus, smooth detection can be realized.

As a method of stacking a number of layers, there is known a method of adjusting the concentration of particles in a particle-dispersed solution or a method of performing similar processes a number of times on the three-dimensional structure adjusted in FIG. 9 that has been obtained by stacking a single layer. Such a method is described in, for example, a document (P. Jiang, et al., Chem. Mater., 1999, 11 (8), 2132.). When such a stacked structure is used, it is also possible to realize a stable structure that is not re-dispersed, by deforming the particles into non-spherical shapes or integrating the particles as in Embodiment 1 or Embodiment 2.

Embodiment 4

Figure 13:
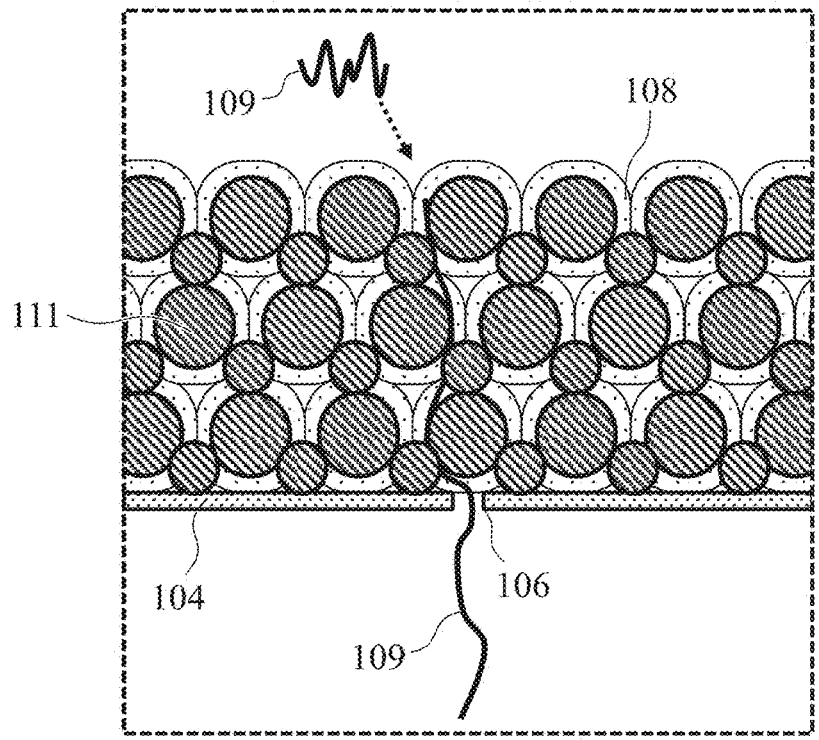
FIG. 13 is a schematic cross-sectional view of a portion around a nanopore of another three-dimensional structure.

FIG. 13 is a schematic cross-sectional view of a portion around a nanopore of a three-dimensional structure with another configuration in a biopolymer analysis device of the present invention. The embodiment shown in FIG. 13 illustrates an example of a three-dimensional structure that is formed using two types of particles with different sizes in FIG. 12. When particles with two different sizes are used, smaller particles will be disposed in voids between larger particles through self-assembly, and thus, the specific surface area is further increased and the probability of adsorption of a biopolymer can thus be increased.

Such a method is described in, for example, a document (K. W. Tan, et al., Langmuir, 2010, 26 (10), 7093.). When such a structure is used, it is also possible to realize a structure that is not re-dispersed in the solution by deforming or integrating the particles as described above. In addition, as the area of contact between the particles is increased, the structure becomes more difficult to be re-dispersed, and thus, the effect of stabilizing the structure is provided. Although an example in which particles with two different sizes are stacked in layers is illustrated herein, it is also possible to use particles with three or more different sizes.

Embodiment 5

Figure 14:
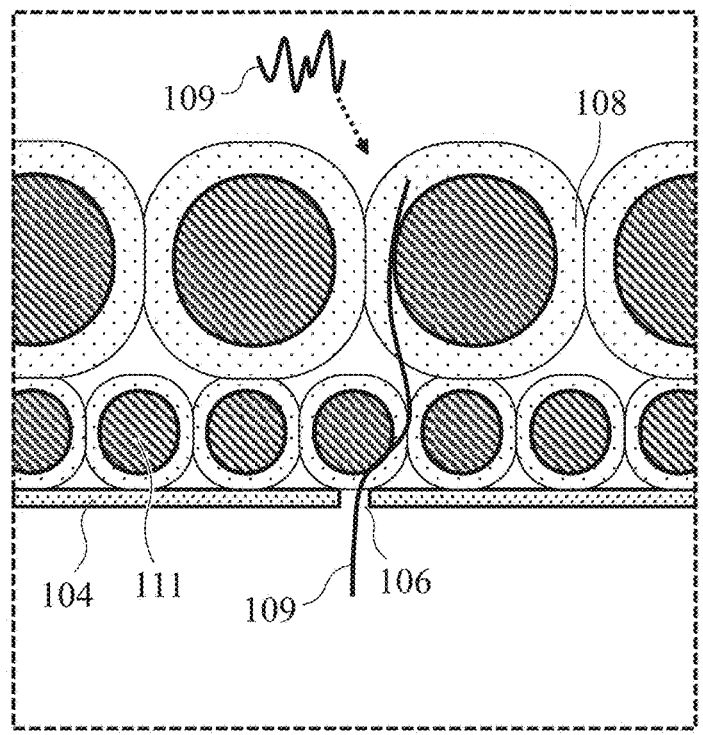
FIG. 14 is a schematic cross-sectional view of a portion around a nanopore of another three-dimensional structure.

FIG. 14 is a schematic cross-sectional view of a portion around a nanopore of a three-dimensional structure with another configuration in a biopolymer analysis device of the present invention. This embodiment is characterized in that a three-dimensional structure with a configuration different from that in FIG. 13 is formed, using two types of particles with different sizes.

FIG. 14 illustrates an example in which smaller particles are stacked as a first layer on a thin film, and larger particles are stacked thereon as a second layer. When particles are arranged in such a manner, it is possible to obtain not only the effect of slowing down the speed of a biopolymer passing through the nanopore but also perform filtering in accordance with the polymer length. A biopolymer with a shorter polymer length can reach the first layer through the second layer as the hydrodynamic radius of the biopolymer is small in a void between the particles of the second layer. However, as a biopolymer with a longer polymer length has a large hydrodynamic radius, a phenomenon occurs in which the biopolymer is adsorbed in a void between large particles of the second layer, and thus does not reach the first layer. Therefore, controlling the sizes of the particles in the first layer and the second layer can selectively detect only a biopolymer with a polymer length in a desired range. It should be noted that a structure in which the particle diameter is gradually increased from the first layer to the uppermost layer is also effective. When such a stacked structure is used, it is also possible to realize a stable structure that is not re-dispersed, by deforming the particles to non-spherical shapes or integrating the particles as in Embodiment 1 or Embodiment 2.

Embodiment 6

Figure 15:
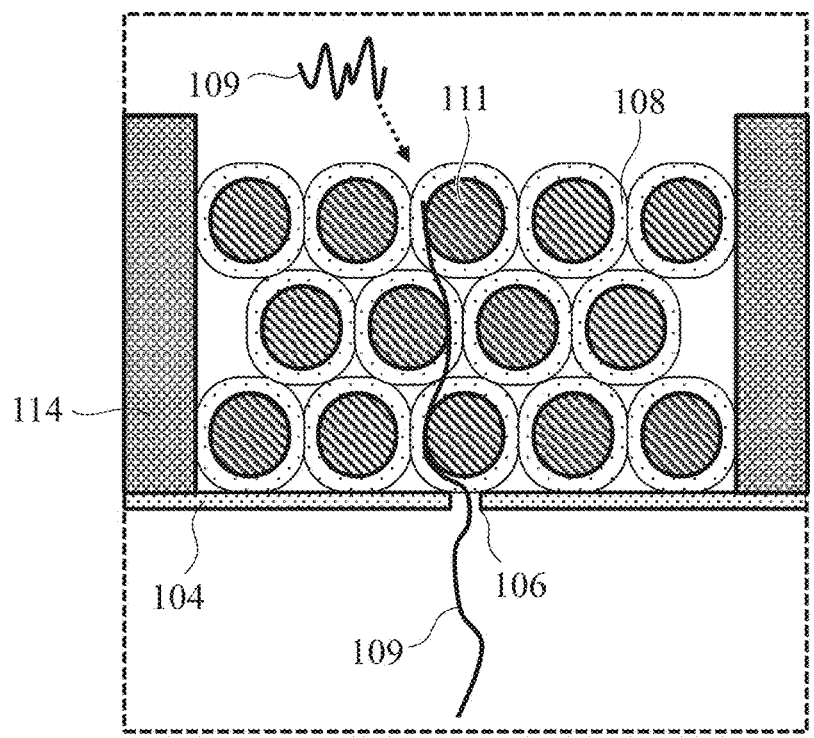
FIG. 15 is a schematic cross-sectional view of a portion around a nanopore of another three-dimensional structure.

FIG. 15 is a schematic cross-sectional view of a portion around a nanopore of a three-dimensional structure with another configuration in a biopolymer analysis device of the present invention. The embodiment shown in FIG. 15 is characterized in that a wall 114 with a thickness greater than that of the three-dimensional structure is provided around the three-dimensional structure shown in FIG. 12, for example.

Providing a wall around the three-dimensional structure has two advantages. The first advantage is that providing a wall around the three-dimensional structure can limit the range of motion of the three-dimensional structure, and thus has the effect of suppressing re-dispersion of the three-dimensional structure into the solution. The second advantage is that increasing the frequency of detection of biopolymers has the effect of reducing the analysis time. When the height and width of the wall are set to about equal to or less than the biopolymer trapping length, the three-dimensional structure can be located in the range of the biopolymer trapping length. According to such a configuration, biopolymers that interact with the structure are concurrently drawn into the nanopore due to a potential gradient. Therefore, the frequency of entry of biopolymers into the nanopore can be increased. In addition to the effect of reducing the analysis time, the effect of being able to detect biopolymers that are contained in a solution at a low concentration can also be obtained. The aforementioned effects can be obtained even when the height and width of the wall surface are greater than the biopolymer trapping length.

Figure 16:
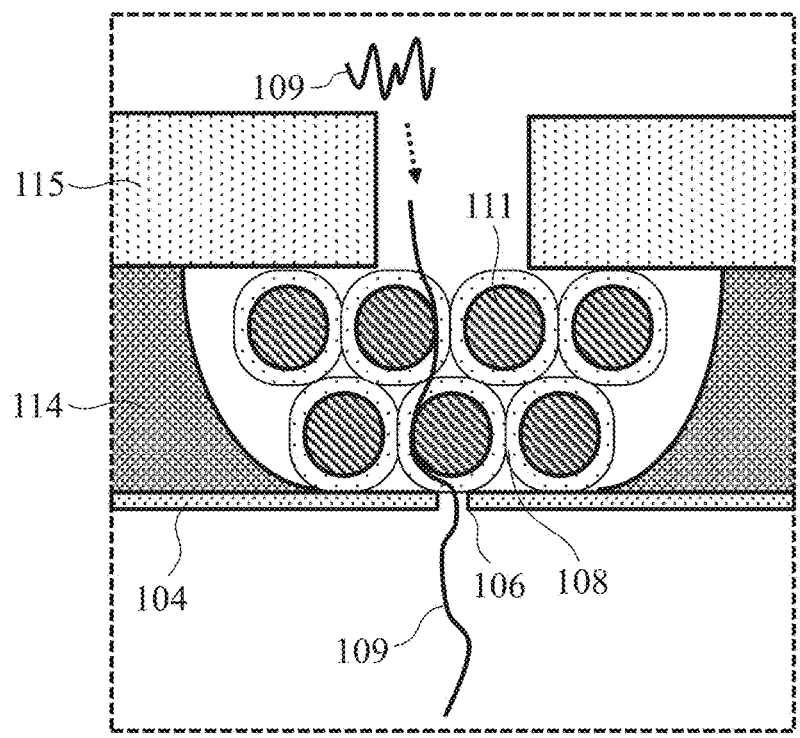
FIG. 16 is a schematic cross-sectional view of a portion around a nanopore of another three-dimensional structure.

Further, as illustrated in FIG. 16, a structure with a second thin film 115, which allows the area of an opening portion of the wall to be smaller than the area of the thin film, is also effective. Providing a structure in which the area becomes smaller toward the solution side in this manner has the effect of limiting the range of motion of the three-dimensional structure more effectively, and thus suppressing re-dispersion of the three-dimensional structure in the solution. Such a structure is described in a document (I. Yanagi, Scientific Reports, 2014, 4, 5000.), and can be produced with the following method, for example. First, a layer of silicon oxide or the like, which is etchable with a hydrofluoric acid solution, is disposed on the thin film 104 having the nanopore 106 formed therein, and then, a layer of a material (e.g., silicon nitride) that is difficult to be etched with the aforementioned solution is disposed. Next, a hole that penetrates the two layers is formed through typical dry etching. If the step is stopped at this point, a structure with a wall such as the one illustrated in FIG. 15 can be produced. Further, performing wet etching using an etchant, such as hydrofluoric acid, can process the etchable layer into a hemispherical shape, and thus can provide a device with a wall structure such as the one illustrated in FIG. 16. At this time, application of particles is performed as the last step using the method described in Embodiment 1.

Embodiment 7

Figure 17:
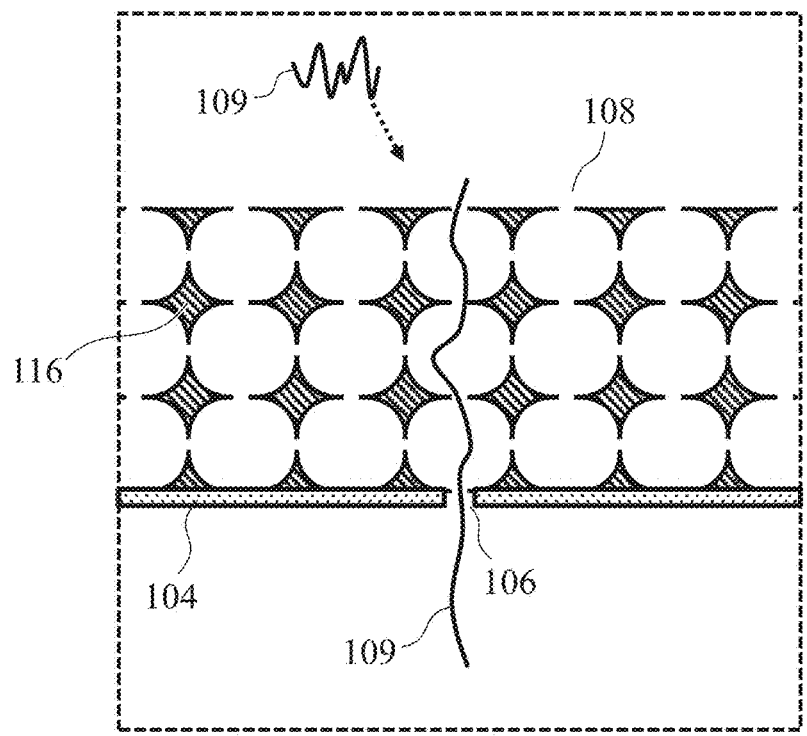
FIG. 17 is a schematic cross-sectional view of a portion around a nanopore of another three-dimensional structure.

FIG. 17 is a schematic cross-sectional view of a portion around a nanopore of a three-dimensional structure with another configuration in a biopolymer analysis device of the present invention. This embodiment is characterized in that a structure that is opposite to those in FIGS. 9 and 12, specifically, an inverted-opal structure, which is obtained by changing the particles to void portions and changing the void portions to a bulk body portion, is used for the three-dimensional structure.

The structure in this embodiment is essentially the same structure as those in FIGS. 9 and 12. Thus, the present structure can also implement the same effects as those described with reference to FIGS. 9 and 12. The inverted-opal structure is described in detail in, for example, a document (J. H. Moon, et al., Chem. Rev., 2010, 110, 547.). The present structure can be obtained with the following method. First, particles are arranged in a regular structure through self-assembly, and then, the particles are not deformed or integrated, but voids between the particles are filled with monomers (which may be either organic or inorganic) so that polymerization reaction is promoted to form a bulk body 116. Next, a process of dissolving and removing the particle portions is performed using a solvent that can dissolve only the particle portions. Finally, in order to form a functional group on the surface of the structure, the structure is immersed in a solution containing a surface treatment agent with high reactivity, such as a silane coupling agent with primary amine, for example, and is then washed with alcohol or the like. An inverted-opal structure formed by using particles as a mold as described above has an advantage in that it is possible to further increase the volume of the solution portion and lower the resistance value while realizing a surface area that is equal to the surface area when the structure is filled with particles. Therefore, a higher ion current value is ensured, and the effect of increasing the measurement sensitivity is thus obtained. As a material used to form the bulk body in the present structure, polystyrene, silica, or the like is preferably used. As the present three-dimensional structure is integrated as a bulk body, it is possible to realize a stable structure that is not re-dispersed in the solution.

In this embodiment, the minimum cross-sectional area of the flow channel refers to the minimum cross-sectional area of voids that form a flow channel connected to the nanopore 106, among the particulate voids used as a mold, in the range of a hemisphere having the biopolymer trapping length r represented by Formula 1 above as the radius. As in Embodiment 1, when particles with a particle diameter of greater than or equal to several nm are used for a mold, it is possible to obtain a cross-sectional area that is greater than or equal to the cross-sectional area of a molecule of a biopolymer. Likewise, the maximum cross-sectional area of the flow channel refers to the maximum cross-sectional area of voids that form a flow channel connected to the nanopore, among the particulate voids used as a mold, in the aforementioned range of the hemisphere. In addition, the maximum cross-sectional area of the voids refers to the maximum cross-sectional area of all particulate voids used as a mold.

Embodiment 8

Figure 18:
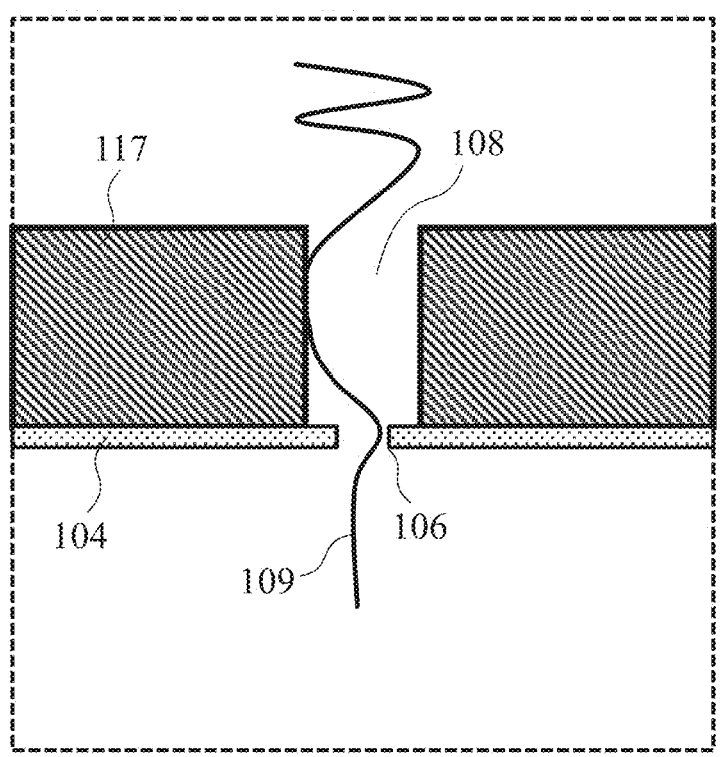
FIG. 18 is a schematic cross-sectional view of a portion around a nanopore of another three-dimensional structure.

FIG. 18 is a schematic cross-sectional view of a portion around a nanopore of a three-dimensional structure with another configuration in a biopolymer analysis device of the present invention. FIG. 18 illustrates, as the simplest example of the three-dimensional structure, an example in which a second thin film 117 having a void is disposed immediately above the nanopore 106 on the first thin film 104 having the nanopore 106.

This embodiment has an advantage in that the cross-sectional area of the void 108 and the thickness of the thin film 117 can be easily controlled, and thus, the probability of adsorption of a biopolymer can be easily controlled. As the void 108, a void with a desired size can be formed through electron beam irradiation. It is also possible to concurrently form the nanopore 106 and the void 108 in the first thin film 104 and the second thin film 117, respectively, in a state in which a nanopore is not formed in the first thin film 104 yet. The second thin film 117 can be formed with a semiconductor microfabrication technique. As a material of such a thin film, a material that can be deposited with a semiconductor microfabrication technique and has a low dielectric constant, such as silicon dioxide, is preferably used so that low capacitance is attained. Reducing the capacitance in this manner can reduce frequency-responsive noise that is dependent on the capacitance when high-frequency measurement is performed, and thus perform stable biopolymer detection. In this embodiment, after the three-dimensional structure is formed, a functional group is formed on the surface thereof through a chemical reaction process as in Embodiment 7. Examples of a method for forming a functional group include immersing the structure in a solution containing a silane coupling agent with primary amine and then washing the structure with alcohol or the like. Using silicon oxide or silicon nitride that does not dissolve in an aqueous solution as a material for the semiconductor microfabrication technique can realize a stable structure that is not re-dispersed in the solution.

In this embodiment, the minimum cross-sectional area of the flow channel refers to the minimum cross-sectional area of the void 108 in the second thin film 117 having the void 108 in the range of a hemisphere having the biopolymer trapping length r represented by Formula 1 above as the radius. Setting the diameter of the void in the second thin film to be greater than or equal to 1 nm can obtain a cross-sectional area that is greater than or equal to the cross-sectional area of a molecule of a biopolymer. Likewise, the maximum cross-sectional area of the flow channel refers to the maximum cross-sectional area of the void 108 in the second thin film 117 having the void 108 in the aforementioned range of the hemisphere. In this embodiment, the cross-sectional area of the flow channel totally coincides with the cross-sectional area of the void.

Embodiment 9

Figure 19:
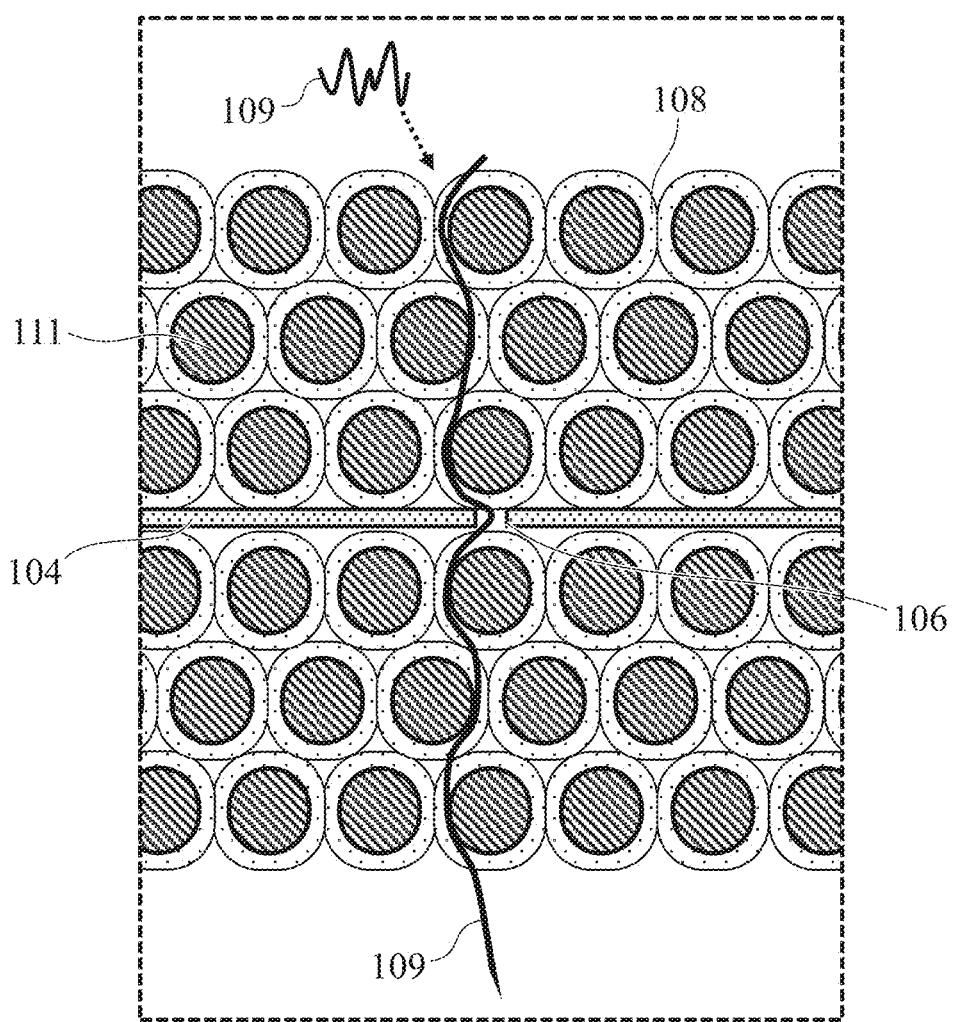
FIG. 19 is a schematic cross-sectional view of a portion around a nanopore of another three-dimensional structure.

FIG. 19 is a schematic cross-sectional view of a portion around a nanopore of a three-dimensional structure with another configuration in a biopolymer analysis device of the present invention. Although the above embodiments each illustrate a case where a three-dimensional structure is disposed on only one side of a thin film, the present embodiment is characterized in that a three-dimensional structure is disposed on each side. Accordingly, the effect of further slowing down the speed of a biopolymer passing through the nanopore can be obtained. FIG. 19 illustrates an example in which the three-dimensional structure illustrated in FIG. 12 is disposed on each side of the thin film 104.

A potential gradient around the nanopore is generated on each of the inlet side and the outlet side. Therefore, disposing a three-dimensional structure on each of the inlet side and the outlet side of the nanopore 106 can reduce a tractive force that acts on the biopolymer 109 on each side and thus realize the effect of further slowing down the speed of a biopolymer passing through the nanopore. Although FIG. 19 illustrates an example in which similar three-dimensional structures are disposed on the opposite sides of the thin film, the three-dimensional structures may be any combination or variation of the structures in the embodiments described with reference to FIGS. 9 to 18. It is also possible to dispose a three-dimensional structure only on the outlet side. When such a stacked structure is used, it is also possible to realize a stable structure that is not re-dispersed, by deforming the particles into non-spherical shapes or integrating the particles as in Embodiment 1 or Embodiment 2.

Embodiment 10

Figure 20:
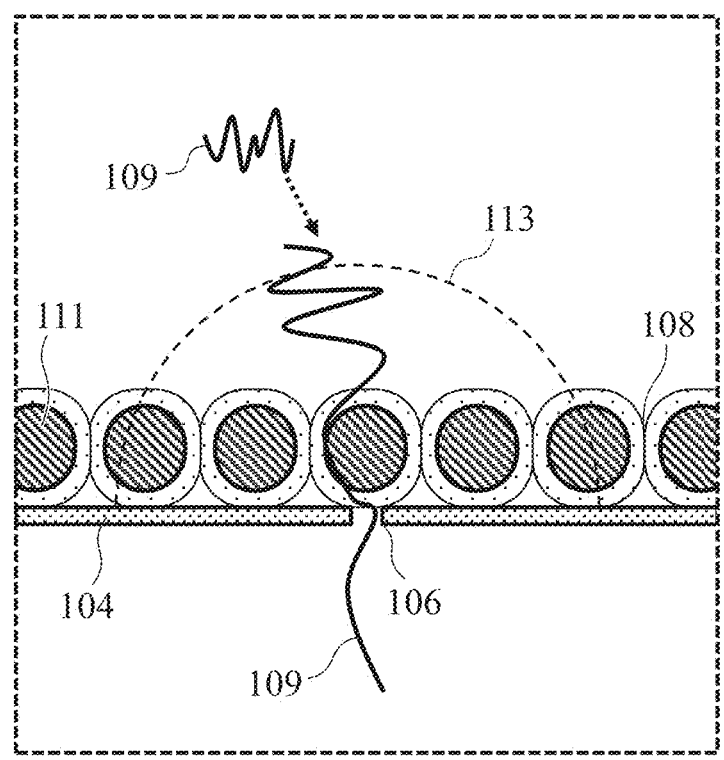
FIG. 20 is a schematic cross-sectional view of a portion around a nanopore of another three-dimensional structure.

FIG. 20 is a schematic cross-sectional view of a portion around a nanopore of a three-dimensional structure with another configuration in a biopolymer analysis device of the present invention. This embodiment is characterized in that the thickness of the three-dimensional structure is less than the biopolymer trapping length. Herein, an embodiment in FIG. 9 is illustrated as an example.

Limiting the thickness of the three-dimensional structure as described above can obtain effects similar to those in Embodiment 6. That is, biopolymers 109 that interact with the three-dimensional structure are concurrently drawn into the nanopore 106 due to a potential gradient. Therefore, the frequency of entry of biopolymers into the nanopore can be increased. In addition to the effect of reducing the analysis time, the effect of being able to detect biopolymers that are contained in a solution at a low concentration can also be obtained. This embodiment can be applied to any of the structures illustrated in FIGS. 9 to 19. The thickness of the three-dimensional structure can be controlled by controlling the particle diameter in the case of FIGS. 9 and 11, controlling the particle diameter and the number of stacked layers in the case of FIGS. 12 to 16 and 19, controlling the particle diameter of the particles to be removed and the number of stacked layer in the case of FIG. 17, and controlling the thickness of the thin film in the case of FIG. 18. When such a stacked structure is used, it is also possible to realize a stable structure that is not re-dispersed, by deforming the particles into non-spherical shapes or integrating the particles as in Embodiment 1 or Embodiment 2.

The definitions of the cross-sectional areas of the flow channel and the voids are the same as those described in Embodiment 1.

Embodiment 11

Figure 21:
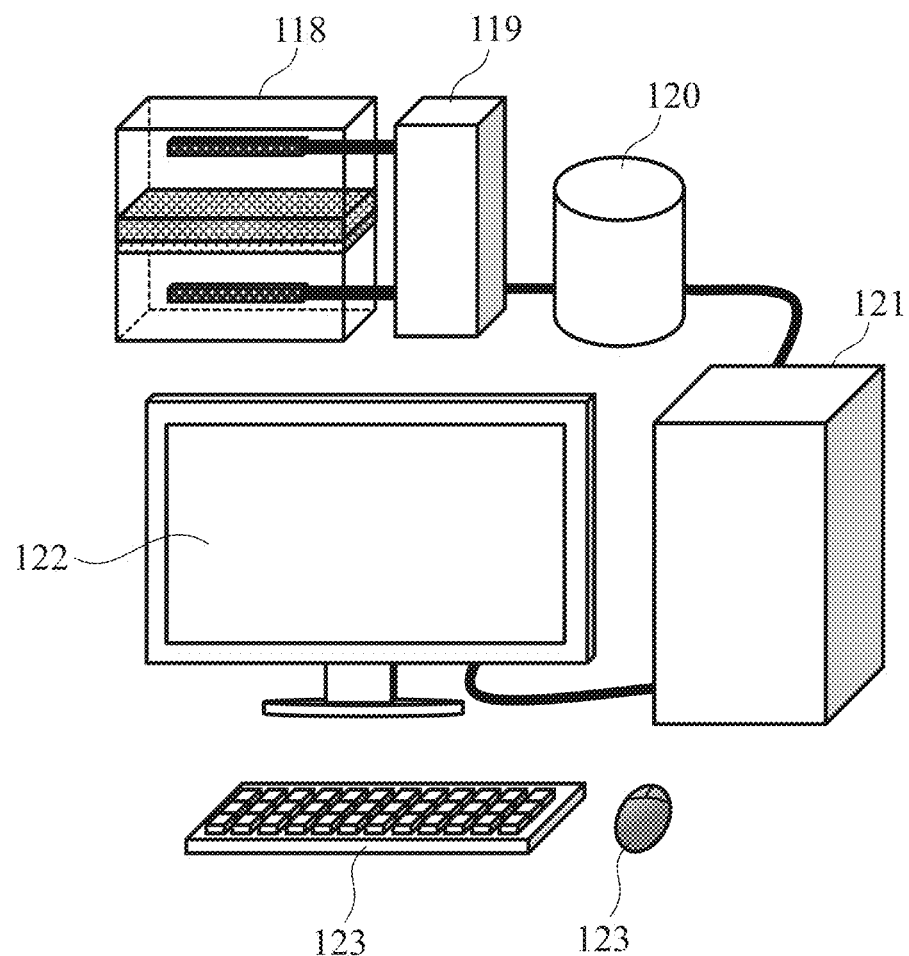
FIG. 21 is a schematic view illustrating an example of a biopolymer analysis system.

FIG. 21 is a schematic view illustrating an example of a biopolymer analysis system using a biopolymer analysis device in accordance with the present invention. The present system typically includes a biopolymer analysis device 118 illustrated in FIG. 1, an ion current measuring device 119 that measures an ion current flowing between a pair of electrodes of the biopolymer analysis device, an analog-digital output conversion device 120 that converts an output signal of the ion current measuring device 119 into a digital signal, a data processing device 121 that processes a signal supplied from the analog-digital output conversion device 120, a data display output device 122 that displays a processing result of the data processing device 121, and an input/output auxiliary device 123. Typically, the ion current measuring device has mounted thereon a high-speed amplification circuit of a current-voltage conversion type, while the data processing device has mounted thereon an arithmetic unit, a temporary storage unit, and a nonvolatile storage unit. In order to reduce the outside noise, the portion of the biopolymer analysis device is preferably covered with a Faraday cage.

Embodiment 12

It is also possible to form a nanopore after disposing a three-dimensional structure on an insulating thin film that does not have a nanopore formed therein yet. A document (I. Yanagi, Scientific Reports, 2014, 4, 5000.) describes a technique capable of forming a nanopore with a desired diameter by continuously applying pulse voltages to an insulating thin film. The three-dimensional structure in this embodiment has a void that is connected to a thin film, and a portion of the void that is in contact with the thin film has the lowest resistance value. Therefore, when the aforementioned pulse voltages are continuously applied to the thin film, the voltages are concentrated in the portion of the void in contact with the thin film, whereby a nanopore can be formed.

Exemplary methods for forming a nanopore in this embodiment include a step of immersing the front and rear surfaces of an insulating thin film, which has disposed thereon a three-dimensional structure with a void that has on its surface a functional group capable of adsorbing a biopolymer, in a solution containing an electrolyte, a step of immersing a pair of electrodes in the solution in which the front surface of the thin film is immersed and in the solution in which the rear surface of the thin film is immersed, and a step of applying pulse voltages across the pair of electrodes. With such a method, a nanopore is formed in the portion where the thin film is in contact with the void.

Figure 22:
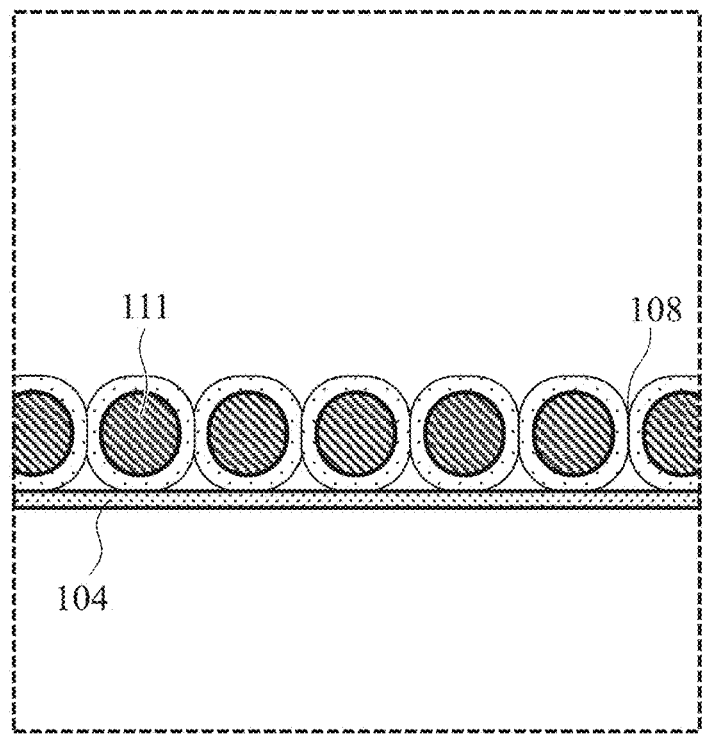
FIG. 22 is a schematic cross-sectional view of a thin film before a nanopore is formed.
Figure 23:
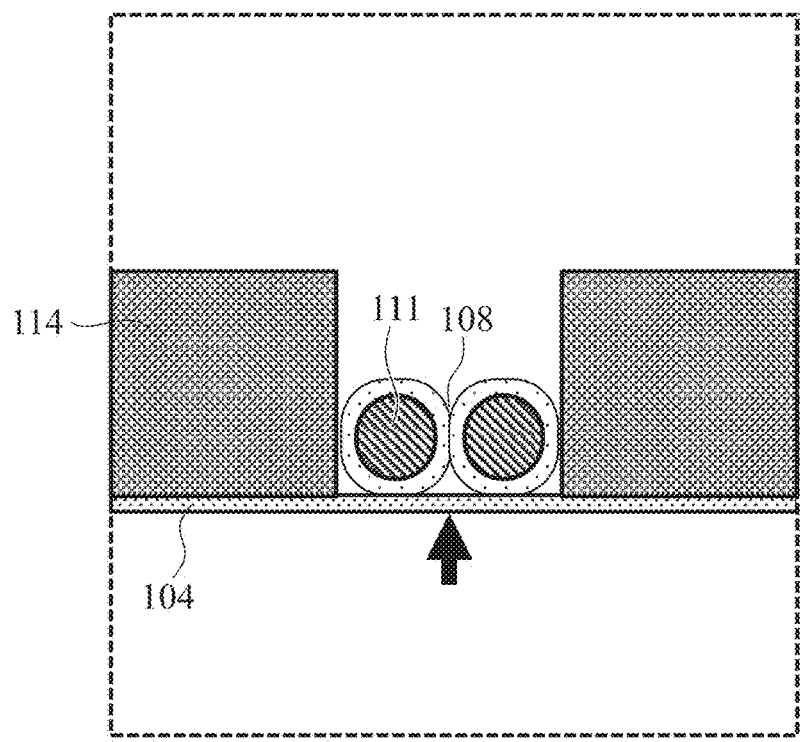
FIG. 23 is a schematic cross-sectional view of a thin film before a nanopore is formed.

As a specific example, FIG. 22 illustrates a case where a thin film 104 having no nanopore formed therein is used in FIG. 9. In this configuration, a nanopore is formed as voltages are concentrated in a portion where the thin film is not in contact with the molded particles, whereby a structure that is the same as that in FIG. 9 can be obtained. In the conventional step of forming an opening through electron beam irradiation, there may be cases where an electron beam may not reach the thin film as the three-dimensional structure becomes a shield. Therefore, the three-dimensional structure is preferably disposed after the step of forming an opening. Using the present step can form a nanopore at any timing, i.e., either before or after the three-dimensional structure is disposed. In addition, controlling the portion of the void that is in contact with the thin film can also control a place where a nanopore is to be formed. For example, as shown in FIG. 23, when a device that has a three-dimensional structure molded from particles and a wall surface exemplarily illustrated in FIG. 15 is used, voltages are concentrated in a portion that is not in contact with the particles and is away from the wall surface, whereby a nanopore can be formed in a place indicated by the arrow. The present step can be applied to any of the structures described in Embodiments 1 to 10 with reference to FIGS. 9 to 20. Due to the reasons described above, a stable device can be supplied in which the three-dimensional structure is not re-dispersed even when a voltage is applied and the structure does not deteriorate after a nanopore is formed.

The definitions of the cross-sectional areas of the flow channel and the voids in this embodiment are the same as those described in Embodiment 1.

Embodiment 13

Figure 24:
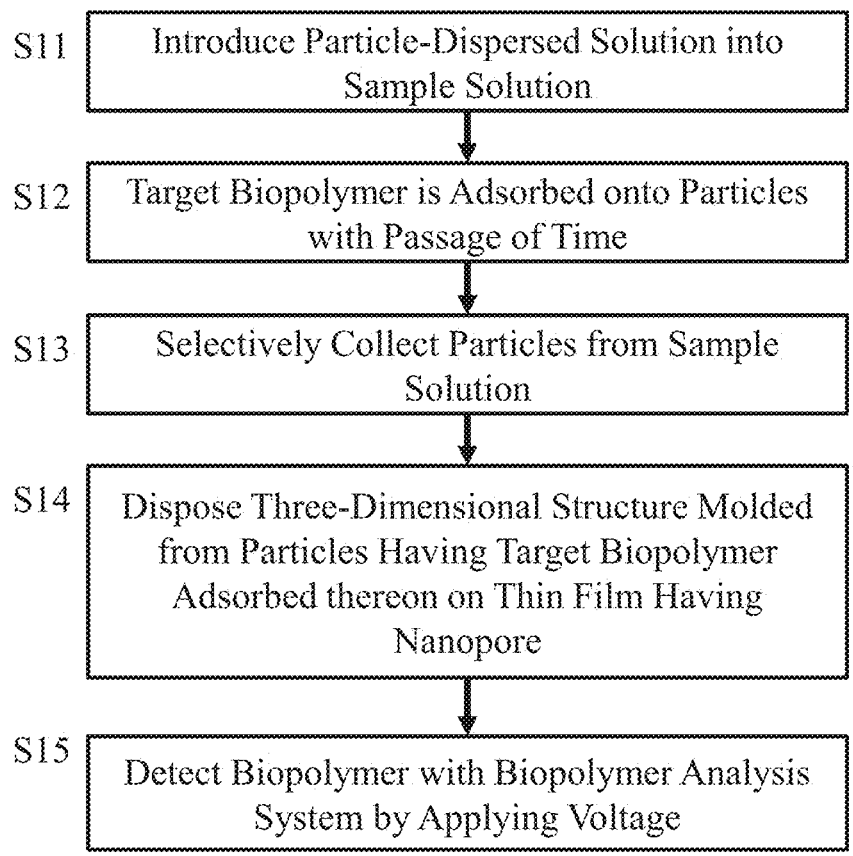
FIG. 24 is a view illustrating an example of an analytical protocol that integrates collection of a sample and slowing down of the speed.
Figure 25:
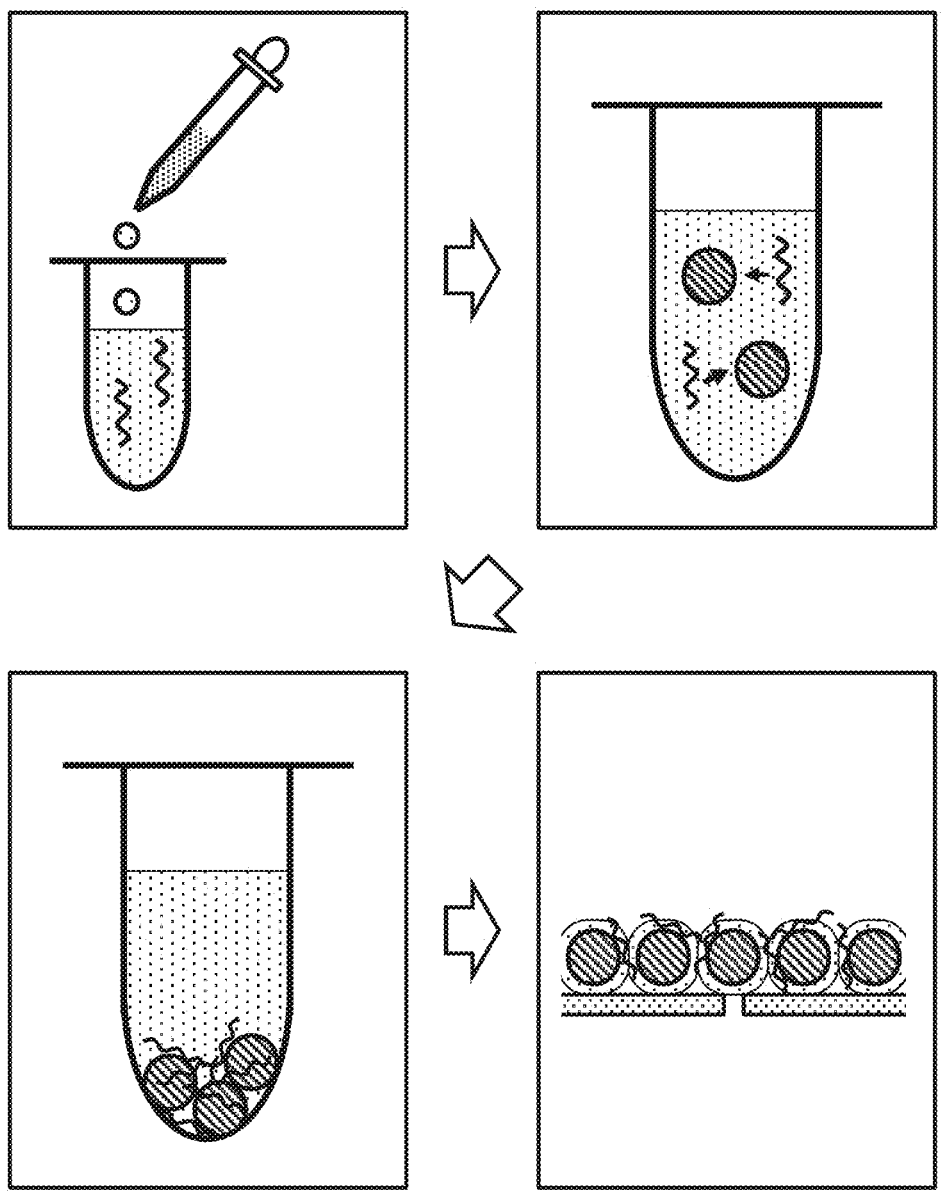
FIG. 25 is a schematic view representing an analytical protocol that integrates collection of a sample and slowing down of the speed.

When a three-dimensional structure is molded using particles, it is possible to implement a biopolymer analysis device that integrates collection of a target biopolymer to be analyzed from a sample and slowing down of the speed of the biopolymer passing through a nanopore. FIG. 24 illustrates a conceptual view of a protocol in this embodiment, and FIG. 25 illustrates a schematic view of the procedures of the protocol.

First, a solution containing dispersed therein particles each having a functional group, which is adapted to adsorb a target biopolymer to be analyzed, is introduced into a sample solution in which the target biopolymer is dissolved (S11). After the solution is introduced, the solution is left for a sufficient time so that the biopolymer can be sufficiently adsorbed onto the surfaces of the particles (S12). After the passage of the sufficient time, only particles that have the target biopolymer adsorbed thereonto are selectively collected using ultracentrifugation (S13). When magnetic particles are used, it is possible to collect only the particles using a magnetic field. After the particles are collected, a three-dimensional structure in FIGS. 9 to 16 or FIG. 19 or 20, which is molded from the particles having the target biopolymer adsorbed thereonto, are disposed on a thin film having a nanopore (S14). Finally, the thus produced device is built into the biopolymer analysis system illustrated in FIG. 21, and a voltage is applied thereto to detect the biopolymer (S15). In this step, magnetic particles, such as ferrite with a paramagnetic property, are preferably used for the particulate substance so that the particles can be smoothly collected.

That is, the analysis method in this embodiment includes a step of collecting a target biopolymer to be analyzed from a sample through adsorption using a plurality of particles each having on its surface a functional group that can adsorb the target biopolymer, a step of disposing a three-dimensional structure, which is molded from the particles and has voids, on a thin film having a nanopore, a step of immersing the thin film having the nanopore in a solution containing an electrolyte and applying a voltage across a pair of electrodes that are arranged with the thin film interposed therebetween, and a step of analyzing the target biopolymer from a change in an ion current when the target biopolymer passes through the nanopore. At this time, the voids in the three-dimensional structure form a flow channel through which the solution containing the electrolyte can pass from the nanopore to a portion above the three-dimensional structure, and the three-dimensional structure is not re-dispersed in the solution at least in the range of a hemisphere having the nanopore as the center and having the biopolymer trapping length r defined by Formula 1 as the radius when a voltage is applied.

In this embodiment, as a biopolymer can be arranged around a nanopore in advance, the detection frequency can be increased. Therefore, the effects of reducing the analysis time and detecting biopolymers contained in a solution at a low concentration are obtained. It should be noted that due to the reasons described in Embodiments 1 to 6, 9, and 10, the three-dimensional structure is not re-dispersed in the solution, and stable measurement can thus be performed. The definitions of the cross-sectional areas of the flow channel and the voids in this embodiment are the same as those described in Embodiment 1.

Embodiment 14

Hereinafter, an example in which a biopolymer is analyzed using the biopolymer analysis system illustrated in FIG. 21 is shown. For the biopolymer analysis device, a device having the three-dimensional structure illustrated in FIG. 15 was used. For the thin film, a thin film made of silicon nitride and having a nanopore with a diameter of 2 nm was used. For the particles, silica nanoparticles with diameters of 100 nm and 50 nm, each having a surface covered with a silanol group, and silica nanoparticles with a diameter of 50 nm, each having a surface covered with a primary amine group, were used. The three-dimensional structure was molded by applying the particles through dip coating and heating and drying them. Meanwhile, as a controlled experiment, an analysis device including only a thin film, which is made of silicon nitride and has a nanopore with a diameter of 2 nm, and including no three-dimensional structure disposed thereon was prepared. For the biopolymer, artificially synthesized polyadenylic acid (polyA) with 5000 bases was used. For the solution, an aqueous solution containing 1 M potassium chloride dissolved therein was used. 1 V was applied as a potential difference to transport the biopolymer.

Figure 26:
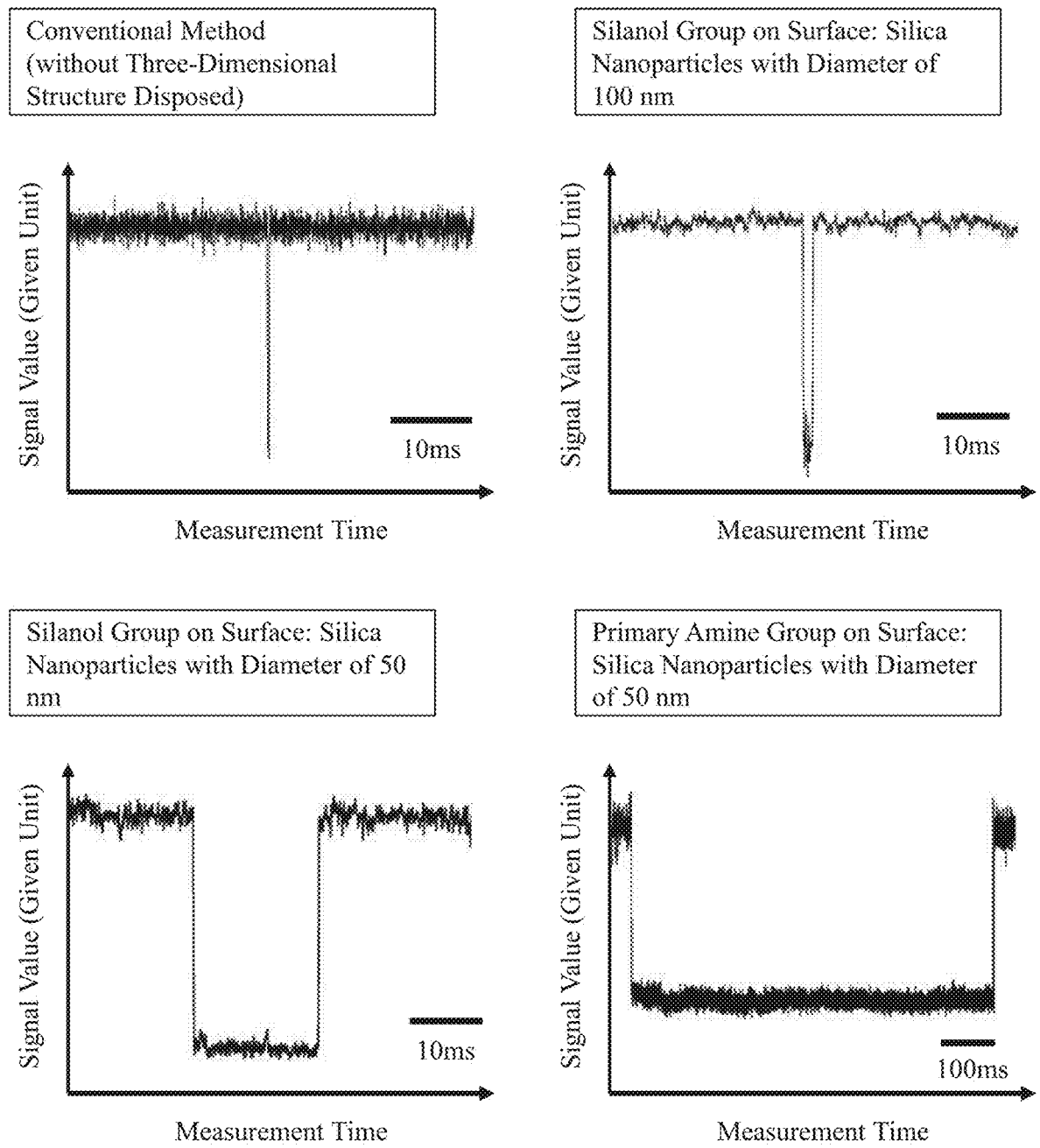
FIG. 26 is a view illustrating typical examples of biopolymer detection.

FIG. 26 shows typical examples of biopolymer detection performed using the biopolymer analysis system in the aforementioned embodiment. In the device without a three-dimensional structure disposed thereon, the typical speed of polyA passing through a nanopore was found to be 0.01 µs/monomer molecule. Meanwhile, in the device having the three-dimensional structure illustrated in FIG. 15 disposed thereon, the speed of polyA passing through a nanopore was found to be 0.46 µs/monomer molecule when silica nanoparticles with a diameter of 100 nm, each having a surface covered with a silanol group, were used, and was found to be 4.6 µs/monomer molecule when silica nanoparticles with a diameter of 50 nm, each having a surface covered with a silanol group, were used. Meanwhile, when silica nanoparticles with a diameter of 50 nm, each having a surface covered with a primary amine group, were used, the speed of polyA passing through a nanopore was found to be 230 µs/monomer molecule. Therefore, it was confirmed that adjusting the conditions to optimal conditions using the device of the present invention can realize a sufficient reduction in the speed of a biopolymer passing through a nanopore by 100 times to 10,000 times in comparison with a case where no three-dimensional structure is used.

When the biopolymer analysis device of the present invention is combined with a monolayer thin film (e.g., graphene) and the solution conditions and analysis conditions disclosed in, for example, a document (A. H. Laszlo, Nature Biotechnology, 2014, Jun. 25), it is possible to sufficiently slow down the speed of a biopolymer, in particular, single-stranded DNA passing through a nanopore, and obtain a signal pattern that depends on a monomer sequence. Performing an analysis based on a signal value, which differs depending on the monomer species, from the obtained signal pattern can analyze a monomer sequence pattern in the biopolymer.

The present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add/remove/substitute a configuration of another embodiment.

REFERENCE SIGNS LIST

101 Tank
102 Solution
103 Three-dimensional structure
104 Thin film
105 Electrode
106 Nanopore
107 Solution inlet port
108 Void
109 Biopolymer
110 Functional group
111 Particle
112 Flow channel
114 Wall
115 Second thin film
116 Bulk body
117 Second thin film having void
118 Biopolymer analysis device
119 Ion current measuring device
120 Analog-digital output conversion device
121 Data processing device

The invention claimed is:

1. A biopolymer analysis device comprising:
two tanks each storing a solution containing a ssDNA or ssRNA and an electrolyte;
a pair of electrodes disposed in the solution within the respective tanks;
a thin film having a nanopore of 0.9 nm -2.0 nm diameter, the thin film being disposed between the two tanks so as to allow the two tanks to communicate with each other via the nanopore; and
a three-dimensional structure disposed on the thin film, the three-dimensional structure being formed from a plurality of layers, each of the layers including a plurality of particles each having on its surface a functional group capable of adsorbing the ssDNA or ssRNA, and the functional group being adapted to be ionized into cations,
wherein:
the functional group that is adapted to be ionized into cations is one of a pyridine group, an imino group, an amine group, an imidazole group, a pyrazole group, or a triazole group,
the three-dimensional structure includes a void,
the void forms a portion of a flow channel, the flow channel being adapted to allow the solution to pass therethrough from the nanopore to a portion above the three-dimensional structure, and the three-dimensional structure having a surface defining the flow channel, the functional group capable of adsorbing the ssDNA or ssRNA being on the surface defining the flow channel, and
the three-dimensional structure is configured to not be re-dispersed in the solution due to at least a tractive force caused by electrophoresis that acts in a direction opposite to an adsorption force in at least a range of a hemisphere having the nanopore as a center and having a ssDNA or ssRNA trapping length r defined by the following formula as a radius, when a voltage is applied across the pair of electrodes:
where:

$$r = \frac{d^2 \mu}{8LD} \Delta V$$

d: diameter of the nanopore

μ: mobility of the ssDNA or ssRNA during electrophoresis

L: thickness of the thin film

D: diffusion coefficient of the ssDNA or ssRNA

V: difference in voltages applied across the pair of electrodes, and a thickness of the three-dimensional structure is less than the ssDNA or ssRNA trapping length.

2. The biopolymer analysis device according to claim 1, wherein a cross-sectional area of the flow channel is greater than or equal to a cross-sectional area of a molecule of the ssDNA or ssRNA and less than or equal to a maximum cross-sectional area of the void.

3. The biopolymer analysis device according to claim 1, wherein a cross-sectional area of the flow channel is greater than or equal to a cross-sectional area of a molecule of the ssDNA or ssRNA and less than or equal to a mean free path S of the ssDNA or ssRNA defined as follows:

$$S=\sqrt{Dt}$$

D: diffusion coefficient of the biopolymer t: mean residence time of the biopolymer in a portion around the nanopore.

4. The biopolymer analysis device according to claim 1, wherein the plurality of particles have non-spherical shapes, and referring to a figure that is obtained by projecting a first particle layer disposed on the thin film onto the thin film from right above the first particle layer, an area occupancy rate of the figure when centers of the plurality of particles form a lattice of an equilateral triangle is greater than $\pi/(12)^{1/2}$ or an area occupancy rate of the figure when centers of the plurality of particles form a lattice of a square is greater than $\pi/4$.

5. The biopolymer analysis device according to claim 1, wherein the plurality of particles are polyhedrons.

6. The biopolymer analysis device according to claim 1, wherein a material of the plurality of particles is one of ceramic or resin.

7. The biopolymer analysis device according to claim 1, wherein the plurality of particles are heated to a temperature of less than or equal to a sintering reaction temperature or a glass transition temperature so that adjacent particles are integrated.

8. The biopolymer analysis device according to claim 1, wherein the three-dimensional structure is molded from two or more types of the plurality of particles, the two or more types of the plurality of particles having different sizes.

9. The biopolymer analysis device according to claim 1, wherein a periphery of the three-dimensional structure is covered with a wall, the wall being thicker than a thickness of the three-dimensional structure.

10. The biopolymer analysis device according to claim 1, wherein the three-dimensional structure is disposed on each side of the thin film.

11. A biopolymer analysis system comprising:

the biopolymer analysis device according to claim 1;

an ion current measuring device configured to measure an ion current flowing between the pair of electrodes of the biopolymer analysis device;

an analog-digital conversion device configured to convert an output signal of the ion current measuring device into a digital signal; and a data processing device configured to process a signal supplied from the analog-digital conversion device.

12. The biopolymer analysis device according to claim 1, wherein the thin film having the nanopore is a first thin film, and the biopolymer analysis device further comprises:

a wall around the three-dimensional structure, the wall having an opening exposing the plurality of particles; and a second thin film disposed on the wall, the second thin film being partially over the plurality of particles exposed by the opening so that the plurality of particles are in a space partially defined by the first thin film, the second thin film and the wall.

13. A biopolymer analysis device comprising:

two tanks each storing a solution containing a ssDNA or ssRNA and an electrolyte;

a pair of electrodes disposed in the solution within the respective tanks;

a thin film having a nanopore of 0.9 nm -2.0 nm diameter, the thin film being disposed between the two tanks so as to allow the two tanks to communicate with each other via the nanopore; and a three-dimensional structure disposed on the thin film, the three-dimensional structure being formed from a plurality of layers, each of the layers including a plurality of particles each having on its surface a functional group capable of adsorbing the ssDNA or ssRNA, and the functional group being a silanol group, wherein the three-dimensional structure includes a void, the void forms a portion of a flow channel, the flow channel being adapted to allow the solution to pass therethrough from the nanopore to a portion above the three-dimensional structure, and the three-dimensional structure having a surface defining the flow channel, the functional group capable of adsorbing the ssDNA or ssRNA being on the surface defining the flow channel, and the three-dimensional structure is configured to not be re-dispersed in the solution due to at least a tractive force caused by electrophoresis that acts in a direction opposite to an adsorption force in at least a range of a hemisphere having the nanopore as a center and having a ssDNA or ssRNA trapping length r defined by the following formula as a radius, when a voltage is applied across the pair of electrodes:

where:

$$r = \frac{d^2\mu}{8LD}\Delta V$$

d: diameter of the nanopore

μ: mobility of the biopolymer during electrophoresis

L: thickness of the thin film

D: diffusion coefficient of the biopolymer

ΔV: difference in voltages applied across the two electrodes.

14. The biopolymer analysis device according to claim 13, wherein the solution contains ions having an chaotropic effect, the ions being one of thiocyanate (SCN$^-$), dihydrogenphosphate ions (H$_2$PO$_4^-$), hydrogen sulfate ion (HSO$_4^-$), bicarbonate ions (HCO$_3^-$), iodide ions (I$^-$), chloride ions (Cl$^-$), nitrate ions (NO$_3^-$), ammonium ions (NH$_4^+$), cesium ions (Cs$^+$), potassium ions (K$^+$), guanidium ions, or tetramethylammonium ions.

15. The biopolymer analysis device according to claim 13, wherein pH of the solution is greater than or equal to 1 and less than or equal to 10.

16. The biopolymer analysis device according to claim 13, wherein an ionic strength of the solution is greater than or equal to 10 mM and less than or equal to an ionic strength of a saturated potassium chloride solution.

* * * * *